(12) United States Patent
Yang-Woytowitz et al.

(10) Patent No.: US 9,834,807 B2
(45) Date of Patent: Dec. 5, 2017

(54) COMPOSITIONS FOR THE DETECTION OF INTRACELLULAR BACTERIAL TARGETS AND OTHER INTRACELLULAR MICORORGANISM TARGETS

(75) Inventors: Mei Yang-Woytowitz, Baltimore, MD (US); Charles Yu, Lutherville, MD (US); Timothy Wiles, Manchester, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 190 days.

(21) Appl. No.: 13/125,017

(22) PCT Filed: Oct. 20, 2009

(86) PCT No.: PCT/US2009/005701
§ 371 (c)(1),
(2), (4) Date: Jul. 13, 2011

(87) PCT Pub. No.: WO2010/047778
PCT Pub. Date: Apr. 29, 2010

(65) Prior Publication Data
US 2011/0262957 A1 Oct. 27, 2011

Related U.S. Application Data

(60) Provisional application No. 61/106,869, filed on Oct. 20, 2008.

(51) Int. Cl.
*C12Q 1/04* (2006.01)
*G01N 33/569* (2006.01)

(52) U.S. Cl.
CPC ......... *C12Q 1/04* (2013.01); *G01N 33/56911* (2013.01)

(58) Field of Classification Search
CPC .............................. C12Q 1/04; G01N 33/56911
See application file for complete search history.

(56) References Cited

U.S. PATENT DOCUMENTS

| | | | |
|---|---|---|---|
| 4,383,032 A | 5/1983 | Stahl et al. | |
| 4,712,310 A | 12/1987 | Roy | |
| 4,740,459 A | 4/1988 | Chen et al. | |
| 4,891,319 A | 1/1990 | Roser | |
| 4,965,193 A | 10/1990 | Chen | |
| 5,338,843 A | 8/1994 | Quante et al. | |
| 5,514,561 A | 5/1996 | Quante et al. | |
| 5,516,902 A | 5/1996 | Quante et al. | |
| 5,583,217 A | 12/1996 | Quante et al. | |
| 5,741,657 A | 4/1998 | Tsien et al. | |
| 5,776,563 A | 7/1998 | Buhi et al. | |
| 5,891,650 A * | 4/1999 | Godowski | C07K 14/705 435/15 |
| 5,922,593 A | 7/1999 | Livingston | |
| 5,955,351 A | 9/1999 | Gerdes et al. | |
| 5,955,604 A | 9/1999 | Tsien et al. | |
| D421,498 S | 3/2000 | Livingston | |
| 6,043,048 A | 3/2000 | Johnston et al. | |
| 6,075,014 A | 6/2000 | Weston et al. | |
| 6,096,272 A | 8/2000 | Clark et al. | |
| 6,284,461 B1 | 9/2001 | Zlokarnik et al. | |
| 6,372,485 B1 | 4/2002 | Clark et al. | |
| 6,472,205 B1 | 10/2002 | Tsien et al. | |
| 6,849,422 B1 | 2/2005 | Wiles et al. | |
| 6,897,304 B2 | 5/2005 | Kawashima et al. | |
| 7,115,384 B2 | 10/2006 | Clark et al. | |
| 7,166,442 B2 | 1/2007 | Black et al. | |
| 7,250,152 B2 | 7/2007 | Gentile et al. | |
| 7,267,962 B2 | 9/2007 | Black et al. | |
| 7,291,480 B2 | 11/2007 | Black et al. | |
| 7,335,485 B2 | 2/2008 | Black et al. | |
| 7,919,294 B2 | 4/2011 | Franco De Sarabia Rosado et al. | |
| 7,927,791 B2 | 4/2011 | Welch et al. | |
| 8,097,434 B2 | 1/2012 | Yang-Woytowitz et al. | |

(Continued)

FOREIGN PATENT DOCUMENTS

GB 2 093 994 A 9/1982
JP S5716699 A 1/1982

(Continued)

OTHER PUBLICATIONS

Ramachandran et al. (Apr. 2006). Dry-reagent storage for disposable lab-on-a-card diagnosis of enteric pathogens. Poster session presented at the 1st Transdisciplinary Conference on Distributed Diagnosis and Home Healthcare (D2H2), Arlington, VA.*
Oberhofer et al., Journal of Clinical Microbiology, vol. 15, No. 2, p. 196-199, 1982.*
Thibodeau et al., Biotechniques, vol. 36, No. 3, p. 410-415, 2004.*
Wang et al., International Journal of Pharmaceutics, vol. 203, No. 1-2, p. 1-60, 2000.*
Elkordy et al., International Journal of Pharaceutics, vol. 278, p. 209-219, 2004.*
Yang et al., Journal of Agricultural and Food Chemistry, vol. 56, No. 2, p. 602-608, 2008; published Dec. 20, 2007.*
Sigma (2-Nitrophenyl beta-D-galactopyranoside, Product Information Sheet, 2008).*

(Continued)

*Primary Examiner* — Rosanne Kosson
(74) *Attorney, Agent, or Firm* — Knobbe, Martens, Olson & Bear, LLP

(57) ABSTRACT

Presented herein are solid supports on or in which a composition comprising a lysis reagent and an intracellular microorganism target detection reagent (e.g., an intracellular bacterial target detection reagent) is present in added form. Presented herein are also methods for detecting the presence of an intracellular microorganism target (e.g., an intracellular bacterial target) utilizing such solid supports. Further, presented herein are tablets as well as dry powders comprising a lysis reagent and an intracellular microorganism target detection reagent (e.g., an intracellular bacterial target detection reagent), and methods of using such tablets and dry powders to detect the presence of an intracellular microorganism target (e.g., an intracellular bacterial target).

23 Claims, No Drawings

(56) References Cited

U.S. PATENT DOCUMENTS

| | | | |
|---|---|---|---|
| 8,389,234 | B2 | 3/2013 | Yang-Woytowitz et al. |
| 9,012,174 | B2 | 4/2015 | Luider et al. |
| 9,085,794 | B2* | 7/2015 | Yang-Woytowitz ..... C12Q 1/04 |
| 2002/0115642 | A1 | 8/2002 | Chan et al. |
| 2003/0119042 | A1 | 6/2003 | De Sarabia Rosado et al. |
| 2004/0115756 | A1 | 6/2004 | Black et al. |
| 2004/0241788 | A1 | 12/2004 | Wainwright et al. |
| 2005/0089947 | A1 | 4/2005 | Black et al. |
| 2005/0244917 | A1 | 11/2005 | Black et al. |
| 2005/0277170 | A1 | 12/2005 | Black et al. |
| 2006/0014230 | A1 | 1/2006 | Murata |
| 2007/0082376 | A1 | 4/2007 | Black et al. |
| 2009/0117601 | A1 | 5/2009 | Yang-Woytowitz et al. |
| 2010/0291543 | A1 | 11/2010 | De Las Heras et al. |
| 2011/0046101 | A1 | 2/2011 | Dmitrienko et al. |
| 2011/0262957 | A1 | 10/2011 | Yang-Woytowitz et al. |
| 2011/0311976 | A1 | 12/2011 | Hanson et al. |
| 2012/0077215 | A1 | 3/2012 | Yang-Woytowitz et al. |
| 2013/0244230 | A1 | 9/2013 | Luider et al. |
| 2014/0080164 | A1 | 3/2014 | Yang-Woytowitz et al. |
| 2016/0138076 | A1 | 5/2016 | Yang-Woytowitz et al. |

FOREIGN PATENT DOCUMENTS

| | | |
|---|---|---|
| JP | S58500150 A | 2/1983 |
| JP | H05-140146 A | 6/1993 |
| JP | 2000-35427 A | 2/2000 |
| JP | 2004-166694 | 6/2004 |
| JP | 2007-501020 | 1/2007 |
| JP | 2010-529976 | 9/2010 |
| RU | 2 240 136 C1 | 11/2004 |
| WO | WO 82/03090 | 9/1982 |
| WO | WO 89/03889 | 5/1989 |
| WO | WO 92/19763 | 11/1992 |
| WO | WO 96/30540 | 10/1996 |
| WO | WO 03/041483 A2 | 5/2003 |
| WO | WO 03/078654 A1 | 9/2003 |
| WO | WO 2004/076054 A2 | 9/2004 |
| WO | WO 2005/040412 A1 | 5/2005 |
| WO | WO 2005/071096 A2 | 8/2005 |
| WO | WO 2006/031936 A2 | 3/2006 |
| WO | WO 2006/43558 A1 | 4/2006 |
| WO | WO 2006/085978 A2 | 8/2006 |
| WO | WO 2006/119280 A2 | 11/2006 |
| WO | WO 2006/121510 A2 | 11/2006 |
| WO | WO 2009/051838 | 4/2009 |
| WO | WO 2009/061864 A1 | 5/2009 |
| WO | WO 2010/004778 | 1/2010 |

OTHER PUBLICATIONS

Babini et al., 2000. "Effect of conalbumin on the activity of Syn 2190, a 1,5 dihydroxy-4-pyridon monobactam inhibitor of AmpC beta-lactamases ," J. of Antimicrob. Chemother., 45: 105-109.

Bebrone et al., 2001, "CENTA as a chromogenic substrate for studying beta-lactamases," Antimicrob. Agents & Chemo. 45(6): 1868-1871.

Birdseee et al., 1967, "Production and ultrastructure of lysozyme and ethylenediammetetraacetate-lysozyme spheroplasts of *Escherichia coli*", Journal of Bacteriology; 93(1):427-437.

Boughton, 1982, "Rapid detection in spinal fluid of beta-lactamase produced by ampicillin-resistant *Ilaemophilus influenzae*," J. of Clinical Microbiol, 15(6): 1167-1168.

Bratu et al., 2005, "Rapid spread of carbapcncm-resistant *Klebsiella pneumoniae* in New York City: A new threat to our antibiotic armamentarium," Arch Intern Med, 165: 1430-1435.

Bush et al., 1995, "A Functional Classification Scheme for β-Lactamases and Its Correlation with Molecular Structure," Antimicrobial Agents and Chemotherapy 39(6): 1211-1233.

Colaco et al., 1992, "Extraordinary stability of enzymes dried in trehalose: simplified molecular biology," Bio/Technology, 10:1007-1011.

Connell, et al., 1994, "Detection of beta lactamase in sputum," J. Clin Pathol, 47: 732-735.

Coudron, 2005, "Inhibitor-based methods for detection of plasmid-mediated AmpC beta-lactamases in *Klebsiella* spp., *Escherichia coli*, and *Proteus mirabilis*," J.Clin. Microbiol., 43(8): 4163-4167.

Database WOI Week 20055, Thomson Scientific, London, GB; Nov. 2004.

Dirama et al., 2006, "Coupling between lysozyme and trehalose dynamics: microscopic insights from molecular-dynamics simulations," J Chem Phys., 124(3):034901-1-034901-8.

Donay et al., 2004, "Evaluation of the automated phoenix system for potential routine use in the clinical microbiology laboratory," J. Clin. Microbiol., 42(4): 1542-1546.

Drawz, et al., 2010, "Three Decades of β-Lactamase Inhibitors," Clinical Microbiology Reviews 23(1): 160-201.

Fiett et al., 2006, "Molecular epidemiology of acquired-metallo-beta-lactamase-producing bacteria in Poland," Antimicrob. Agents & Chemo., 50(3): 880-886.

Hanaki et al., 2004, "Characterization of HMRZ-86: a novel chromogenic cephalosporin for the detection of extended-spectrum beta-lactamases," J. Antimicro. Chemo. Advance Access Pub., 53(5):888-889.

Hanson. 2003, "AmpC heta-lactamases: what do we need to know for the future," J. Antimicrob. Chemother., 52: 2-4.

Hedoux et al., 2006, "Analysis of sugar bioprotective mechanisms on the thermal denaturation of lysozyme front Raman scattering and differential scanning calorimetry investigations," J Phys Chem B. 110(45):22886-93.

International Search Report of application PCT/US2008/011934, dated Jan. 19, 2009.

International Search Report of International application PCT/US2009/005701, dated Mar. 30, 2010.

Jacoby et al., 2005, "The new beta-lactamases," The New England J. of Med., 352(4): 380-391.

Jamieson et al,. 2003, "In vitro and in vivo activities of AM-112, a novel oxapenem," Antimicro Agents & Chemo., 47(5): 1652-1657.

Jiang et al 2006., "Detection of extended-spectrum beta-lactamases in clinical isolates of *Pseudomonas aeruginosa*," Antimicro Agents & Chemo., 50(9): 2990-2995.

Jones et al., 1982. "In vitro evaluation of CENTA, a new beta-lactamase-susceptible chromogenic cephalosporin reagent," J. of Clinical Micro., 15(5): 954-958.

Jovanovic et al., 2004, "Stabilization of proteins in dry powder formulations using supercritical fluid technology," Pharm Res., 21(11):1955-1969.

Jovanovic et al., 2006, "Distinct effects of sucrose and trehalose on protein stability during supercritical fluid drying and freeze-drying," Eur J Pharm. Sci., 27(4):336-45.

Jovanovic et al., 2006, "Near-infrared imaging for studying homogeneity of protein-sugar mixtures," Pharm. Res., 23(9):2002-2013.

Jovanovic et al., 2008, "Stable sugar-based protein formulations by supercritical fluid drying." Intl J. Pharm., 346(1-2):102-8.

Kaushik et al., 2003, "Why is trehalose an exceptional protein stabilizer? An analysis of the thermal stability of proteins in the presence of the compatible osmolyte trehalose", J Biol Chem: 278(29):26458-26465.

Lerbret et al., 2007. "How do trehalose, maltose, and sucrose influence some structural and dynamical properties of lysozyme? Insight from molecular dynamics simulations," J Phys Chem. B., 111(31):9410-20.

Liao et al., 2002. "Effects of sucrose and trehalose on the preservation of the native structure of spray-dried lysozymc," Pharm Res., 19(12):1847-1853.

Liao et al., 2002, "Protective mechanism of stabilizing excipients against dehydration in the freeze-drying of proteins," Pharm Res., 19(12):1854-1861.

Liao et al., 2003, "Investigation of the physical properties of spray-dried stabilised lysozyme particles." J Pharm Pharmacol., 55(9): 1213-21.

Liao et al., 2004. "Investigation of the stabilisation of freeze-dried lysozyme and the physical properties of the formulations," Eur J. Pharm Biopharm., 58(1):15-24.

(56) References Cited

OTHER PUBLICATIONS

Livermore et al., 2006, "The beta-lactamase threat in enterobacteriaceae, pseudomonas and acinetobacter," Trends in Microbiol, 14(9): 413-420.
Marchiaro et al., 2005, "Sensitive EDTA-based microbiological assays for detection of metallo-beta-lactamases in nonfermentative gram-negative bacteria," J. of Clinical Microbiol., 43(11): 5648-5652.
Martin et al., 1990, "Increase in the activity of third-generation cephalosporins in combination with clavulanic acid and Sulbactam™ against *Bacteraides fragilis*," Med Lab Sciences, 47: 163-167.
Martin et al., 1991, "A comparative study of the activity of first and second generation of cephalosporins and their combinations with beta-lactamase inhibitors against *Bacteroides fragilis*," Microbios, 67: 195-202.
Miller et al., 2001, "Beta-lactamase-inhibitor combinations in the $21^{st}$ century current agents and new developments," Current Opinion of Pharmacology, 1(5): 451-458.
Moland et al., 2006, "Prevalence of newer beta-lactamases in gram-negative clinical isolates collected in the United States from 2001 to 2002," J. of Clinical Microbiol, 44(9): 3318-3324.
Nukaga, et al., 2003, "Inhibition of class A and class C beta-lactamases by penems: crystallographic structures of a novel 1,4-thiazepine intermediate," Biochem, 42: 13152-13159.
O'Callaghan et al., 1972, "Novel method for detection of beta-lactamases by using a chromogenic cephalosporin substrate," Antimicro Agents & Chemo, 1(4): 283-288.
Papanicolaou et al., 1990, "Discrimination of extended-spectrum beta-lactamases by a novel nitrocefin competition assay," Antimicro Agents & Chemo, 34(11): 2184-2192.
Payne et al., 1994. "Rapid identification of metallo- and serine beta-lactamases," Antimicro Agents & Chemo, 38(5): 991-996.
Petropoulou et al., 2006. "Evaluation of imipenem/imipenem+EDTA disk method for detection of metallo-beta-lactamase-producing *Klebsiella pneumoniae* isolated from blood cultures," Microbiol Drug Resistance, 12(1): 39-43.
Philippon et al., 2002, "Plasmid-determined AmpC-type beta-lactamases," Antimicrob. Agents Chemother, 46: 1-11.
Queenan et al.. 2007, "Carbapenemases: the versatile beta-lactamases," Clinical Microbiology Review, 20(3): 440-458.
Ramachandran et al., 2006, "Dry-reagent storage for disposable lab-on-a-card diagnosis of enteric pathogens," Proceedings of the $1^{st}$ Distributed Diagnosis & Home Healthcare (D2H2) Conference, Arlington, VA—IEEE, pp. 16-19.
Rasheed et al., 2000, "Characterization of the extended-spectrum beta-lactamase reference strain, *Klebsiella pneumoniae* K6 (ATCC 700603), which produces the novel enzyme SHV-18," Antimicrob. Agents Chem. Ther. 44: 2382-2388.
Reig et al., 1991,"[Characterization of Haemophilus influenzae's resistance to ampicillin]," Med Clin (Bare), 96: 727-729.
Sanders et al., 1986. "Characterization of beta-lactamases in situ on polyacrylamide gels," Antimicro Agents & Chemo., 30(6): 951-952.
Shannon et al., 1980, "Beta-lactamase detection by three simple methods: Intralactam, nitrocefin and acidimetric," J. Antimicrobiol Chemo., 6: 617-621.
Sharma et al., 2004, "Detection and assay of beta lactamases in clinical and non-clinical strains of Yersinia enterocolitica biovar 1A", J Antimicrob Chemother; 54(2):401-405.
Singh et al., 2003. "Effect of polyols on the conformational stability and biological activity of a model protein lysozyme", AAPS PharmSciTech, 4(3):article 42: 1-9.
Thomson et al., 2006, "Comparison of phoenix and vitek 2 ESBL confirmatory tests against *E. coli* and *Klebsiella* isolates with well-characterized beta-lactamases," 106th General Meeting of the American Society for Microbiology, Orlando, FL 2006.
Turner et al., 2000, "Detection of ESBL producing *E. coli and Klebsiella* in the Phoenix™ automated microbiology system," $10^{th}$ European Congress of Clinical Microbiology & Infectious Diseases, May 2000.
URI, 1985, "Detection of beta-lactamase activity with nitrocetin of multiple strains of various microbial genera," Acta Micro Hungarica, 32(2): 133-145.
Walsh et al., 2005, "Metallo-beta-lactamases: the quiet before the storm?" Clinical Microbiol Reviews, 18( 2): 306-325.
Walsh, 2005, "The emergence and implications of metallo-beta-lactamases in Gram-negative bacteria," Clinical Microbiol & Infect. Disc., 11(Supp. 6): 2-9.
Written Opinion of International application PCT/US2008/011934, dated Jan. 19, 2009.
Written Opinion of International application PCT/US2009/005701, dated Mar. 30. 2010.
Yigit et al., 2001, "Novel carbapenem-hydrolyzing beta-lactamase, KPC-1, from a carbapenem-resistant strain of *Klebsiella pneumoniae*," Antimicrob. Agents Chemother., 45: 1151-1161.
Yigit et al., 2003, "Carbapenem-resistant strain of *Klebsiella oxytoca* harboring carbapenem-hydrolyzing beta-lactamase KPC-2," Antimicrob. Agents & Chemother., 47: 3881-3889.
Yong et al., 2006, "Increasing prevalence and diversity of metallo-beta-lactamases in *Pseudomonas* spp., *Acinerobucter* spp., and *Enterobacteriuceae* from Korea," Antimicro Agents & Chemo, 50(5): 1884-1886.
Yu et al., 1999, "Rapid detection of heta-lactamase production in penicillin sensitive staphylococci by the Phoenix™ automated ID/AST system," $9^{th}$ European Congress of Clinical Microbiology & Infection Disease, Berlin, Germany, Mar. 1999.
U.S. Appl. No. 60/981,156, filed Oct. 19, 2007, Yang et al.
Issue Fee Transmittal of U.S. Appl. No. 13/307,426, dated Jan. 30, 2013.
BD—BBL™ DrySlide™ Nitrocefin Product Information; revision date: Jun. 1, 2010.
BD—BBL™ DrySlide™ Nitrocefin Package Insert ; revision Jun. 2010.
BD—Microbiology Identification and Susceptibility Solutions brochure, dated Dec. 2008.
BD—DrySlide™The Dry Alternative in Rapid Testing promotional flyer, dated Oct. 2009.
Notice of Allowance and Fees Due of U.S. Appl. No. 13/307,426, dated Oct. 31, 2012.
Office Action of U.S. Appl. No. 13/307,426, dated May 17, 2012.
Response to Non-Final Rejection dated May 17, 2012, dated Sep. 17, 2012.
Elkordy et al., 2002, "Integrity of crystalline lysozyme exceeds that of a spray-dried form", International Journal of Pharmaceutics, 247:79-90.
Jain et al., 2007, "Rapid detection of extended-spectrum β-lactamase-producing Gram-negative bacilli in blood cultures," Journal of Antibicrobial Chemotherapy, 60:652-654.
Pitkälä et al., "Comparison of Tests for Detection of Beta-Lactamase-Producing Staphylococci," J Clin Microbiol. (Apr. 2007) 45(6): 2031-2033.
Chopra et al., 1985, "Inhibition of beta-lactamase synthesis in *Staphylococcus aureus* by minocycline", J Antimicrob Chemother. 16: 17-21.
Leonard et al., 1995, "Comparison of MIDI Sherlock System and Pulsed-Field Gel Electrophoresis in Characterizing Strains of Methicillin-Resistant *Staphylococcus aureus* from a Recent Hospital Outbreak", J Clin Microbiol. 44(10): 2723-2727.

\* cited by examiner

COMPOSITIONS FOR THE DETECTION OF INTRACELLULAR BACTERIAL TARGETS AND OTHER INTRACELLULAR MICORORGANISM TARGETS

This application is a national stage application of International Patent Application No. PCT/US2009/005701, filed Oct. 20, 2009, which claims priority under 35 U.S.C. §119(e) to U.S. provisional patent application No. 61/106,869, filed Oct. 20, 2008. each of which is incorporated herein by reference in its entirety.

1. INTRODUCTION

Presented herein are solid supports on or in which a composition comprising a lysis reagent and an intracellular microorganism target detection reagent (e.g., an intracellular bacterial target detection reagent) is present in a dried form. Presented herein are also methods for detecting the presence of an intracellular microorganism target (e.g., an intracellular bacterial target) utilizing such solid supports. Further, presented herein are tablets as well as dry powders comprising a lysis reagent and an intracellular microorganism target detection reagent (e.g., an intracellular bacterial target detection reagent), and methods of using such tablets and dry powders to detect the presence of an intracellular microorganism target (e.g., an intracellular bacterial target).

2. BACKGROUND

Detection of intracellular bacterial enzymes is typically performed by preparing a suspension of bacterial cells, mixing the bacterial cell suspension with lysis buffer for a period of time, preparing the reagents needed to detect an intracellular bacterial enzyme and adding those reagents to the bacterial extract formed from lysing the bacterial cells. This process requires the preparation of multiple solutions and multiple steps.

3. SUMMARY

In one aspect, presented herein are solid supports containing a dry composition which provides reagents for lysing a microorganism and reagents for detection of an intracellular microorganism target. In one embodiment, presented herein are solid supports containing a dried composition which provides reagents necessary to lyse a microorganism as well as reagents necessary to detect an intracellular microorganism target. In a specific embodiment, the solid supports contain a dried composition which provides all of the reagents necessary to lyse a microorganism as well as all of the reagents necessary to detect an intracellular microorganism target. The solid supports presented herein can eliminate the multiple steps of sample preparation required for the detection of an intracellular microorganism target, and thus, reduce the time needed to detect an intracellular microorganism target. In a specific embodiment, the solid supports presented herein provide a one-step process for the detection of an intracellular microorganism target. Further, the dried compositions contained in or on the solid supports described herein can be stable for extended periods of time at, e.g., room temperature.

In a specific embodiment, presented herein are solid supports containing a dried composition, wherein the composition comprises a lysis reagent and an intracellular microorganism target detection reagent. In accordance with this embodiment, the dry composition may be present in or on the solid supports. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are solid supports containing a dried composition which provides reagents necessary to lyse a bacterial cell as well as reagents necessary to detect an intracellular bacterial target. In a specific embodiment, the solid supports contain a dried composition which provides all of the reagents necessary to lyse a bacterial cell as well as all of the reagents necessary to detect an intracellular bacterial target. The solid supports presented herein can eliminate the multiple steps of sample preparation required for the detection of an intracellular bacterial target, and thus, reduce the time needed to detect an intracellular bacterial target. In a specific embodiment, the solid supports presented herein provide a one-step process for the detection of an intracellular bacterial target. Further, the dried compositions contained in or on the solid supports described herein can be stable for extended periods of time at, e.g., room temperature.

In a specific embodiment, presented herein are solid supports containing a dried composition, wherein the composition comprises a lysis reagent and an intracellular bacterial target detection reagent. In accordance with this embodiment, the dry composition may be present in or on the solid supports. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In one embodiment, the solid support containing a dried form of a composition described herein is a well of a tray, plate, panel or cassette. In another embodiment, the solid support containing a dried form of a composition described herein is a paper disk or a paper strip. In another embodiment, the solid support containing a dried form of a composition described herein is a tube.

In another aspect, presented herein are methods for detecting the presence of an intracellular microorganism target using a solid support containing a dry composition which provides reagents for lysing a microbe as well as reagents for the detection of an intracellular microorganism target. In accordance with this aspect, the dry composition may be present in or on the solid support. In one embodiment, presented herein are methods for detecting the presence of an intracellular microorganism target using a solid support containing a dried composition which provides reagents necessary to lyse a microbe as well as reagents necessary to detect an intracellular microorganism target. In a specific embodiment, a method for detecting the presence of an intracellular microorganism target comprises (a) contacting a microorganism sample with a solid support containing a dried composition, wherein the composition comprises a lysis reagent and an intracellular microorganism target detection reagent; and (b) detecting utilization of the intracellular microorganism target detection reagent, wherein utilization of the intracellular microorganism target detection reagent indicates the presence of an intracellular microorganism target. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are methods for detecting the presence of an intracellular bacterial target using a solid support containing a dried composition which provides reagents necessary to lyse a bacterial cell as well as reagents necessary to detect an intracellular bacterial target. In one embodiment, a method for detecting the presence of an intracellular bacterial target comprises (a) contacting a bacterial sample with a solid support containing a dried composition, wherein the composition comprises a lysis reagent and an intracellular bacterial target detection reagent; and (b) detecting utilization of the intracellular bacterial target detection reagent, wherein utilization of the intracellular bacterial target detection reagent indicates the presence of an intracellular bacterial target. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In another aspect, presented herein are kits for use in detecting the presence of an intracellular microorganism target, wherein the kits comprise a solid support containing a dry composition which provides reagents for lysing a microbe as well as reagents for the detection of an intracellular microorganism target. In accordance with this aspect, the dry composition may be present in or on the solid support. In one embodiment, presented herein are kits for use in detecting the presence of an intracellular microorganism target, wherein the kits comprise a solid support containing a dried composition which provides reagents necessary to lyse a microbe as well as reagents necessary to detect an intracellular microorganism target. In a specific embodiment, presented herein is a kit comprising, in a container, a solid support containing a dried composition, wherein the composition comprises a lysis reagent and an intracellular microorganism target detection reagent. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent. The solid support containing a dried composition described herein may be, e.g., a well of a tray, a plate, a panel or a cassette, a paper disk, a paper strip, or a tube (e.g., a test tube or Eppendorf tube).

In a specific aspect, presented herein are kits for use in detecting the presence of an intracellular bacterial target, wherein the kits comprise a solid support containing a dried composition which provides reagents necessary to lyse a bacterial cell as well as reagents necessary to detect an intracellular bacterial target. In a specific embodiment, presented herein is a kit comprising, in a container, a solid support containing a dried composition, wherein the composition comprises a lysis reagent and an intracellular bacterial target detection reagent. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent. The solid support containing a dried composition described herein may be a well of a tray, a plate, a panel or a cassette, a paper disk, a paper strip, or a tube (e.g., a test tube or Eppendorf tube).

In another aspect, presented herein are compositions comprising a lysis reagent and an intracellular microorganism target detection reagent in the form of a dry powder. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a bacterial cell by a lysis reagent.

In a specific aspect, presented herein are compositions comprising a lysis reagent and an intracellular bacterial target detection reagent in the form of a dry powder. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In another aspect, presented herein are methods for detecting the presence of an intracellular microorganism target using a composition in the form of a dry powder, wherein the composition comprises a lysis reagent and an intracellular bacterial target detection reagent. In one embodiment, presented herein is a method for detecting the presence of an intracellular microorganism target comprising (a) contacting a microorganism sample with a composition in the form of a dry powder, wherein the composition comprises a lysis reagent and an intracellular microorganism target detection reagent; and (b) detecting utilization of the intracellular microorganism target detection reagent, wherein utilization of the intracellular microorganism target detection reagent indicates the presence of an intracellular microorganism target. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are methods for detecting the presence of an intracellular bacterial target using a composition in the form of a dry powder, wherein the composition comprises a lysis reagent and an intracellular bacterial target detection reagent. In one embodiment, presented herein is a method for detecting the presence of an intracellular bacterial target comprising (a) contacting a bacterial sample with a composition in the form of a dry powder, wherein the composition comprises a lysis reagent and an intracellular bacterial target detection reagent; and (b) detecting utilization of the intracellular bacterial target detection reagent, wherein utilization of the intracellular bacterial target detection reagent indicates the presence of an intracellular bacterial target. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In another aspect, presented herein are kits for use in detecting the presence of an intracellular microorganism target, wherein the kits contain a composition in the form of a dry powder that comprises a lysis reagent and an intracellular microorganism target detection reagent. In one embodiment, a kit comprises a composition in the form of a dry powder, wherein the composition comprises a lysis reagent and an intracellular microorganism target detection reagent, and, optionally, instructions for use. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are kits for use in detecting the presence of an intracellular bacterial target, wherein the kits contain a composition in the form of a dry powder that comprises a lysis reagent and an intracellular bacterial target detection reagent. In one embodiment, a kit comprises a composition in the form of a dry powder, wherein the composition comprises a lysis reagent and an intracellular bacterial target detection reagent, and, optionally, instructions for use. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In another aspect, presented herein are tablets comprising a composition, wherein the composition comprises a lysis reagent and an intracellular microorganism target detection reagent. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are tablets comprising a composition, wherein the composition comprises a lysis reagent and an intracellular bacterial target detection reagent. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In another aspect, presented herein are methods for detecting the presence of an intracellular microorganism target using a tablet comprising a composition, wherein the composition comprises a lysis reagent and an intracellular microorganism target detection reagent. In one embodiment, presented herein is a method for detecting the presence of an intracellular microorganism target comprising (a) contacting a microorganism sample with a tablet comprising a composition, wherein the composition comprises a lysis reagent and an intracellular microorganism target detection reagent; and (b) detecting utilization of the intracellular microorganism target detection reagent, wherein utilization of the intracellular microorganism target detection reagent indicates the presence of an intracellular microorganism target. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are methods for detecting the presence of an intracellular bacterial target using a tablet comprising a composition, wherein the composition comprises a lysis reagent and an intracellular bacterial target detection reagent. In one embodiment, presented herein is a method for detecting the presence of an intracellular bacterial target comprising (a) contacting a bacterial sample with a tablet comprising a composition, wherein the composition comprises a lysis reagent and an intracellular bacterial target detection reagent; and (b) detecting utilization of the intracellular bacterial target detection reagent, wherein utilization of the intracellular bacterial target detection reagent indicates the presence of an intracellular bacterial target. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

In another aspect, presented herein are kits for use in detecting the presence of an intracellular microorganism target, wherein the kits contain a tablet comprising a lysis reagent and an intracellular microorganism target detection reagent. In one embodiment, a kit comprises a tablet, wherein the tablet comprises a composition comprising a lysis reagent and an intracellular microorganism target detection reagent, and, optionally, instructions for use. In some embodiments, the composition further comprises an agent that promotes the stabilization of the lysis reagent. In other embodiments, the composition further comprises an agent that enhances the lysis of a microbe by a lysis reagent. In other embodiments, the composition further comprises an agent that promotes the stabilization of the lysis reagent and an additional agent, e.g., an agent that enhances the lysis of a microbe by a lysis reagent.

In a specific aspect, presented herein are kits for use in detecting the presence of an intracellular bacterial target, wherein the kits contain a tablet comprising a lysis reagent and an intracellular bacterial target detection reagent. In one embodiment, a kit comprises a tablet, wherein the tablet comprises a composition comprising a lysis reagent and an intracellular bacterial target detection reagent, and, optionally, instructions for use. In some embodiments, the composition further comprises an agent that promotes the stabilization of the lysis reagent. In other embodiments, the composition further comprises an agent that enhances the lysis of a bacterial cell by a lysis reagent. In other embodiments, the composition further comprises an agent that promotes the stabilization of the lysis reagent and an additional agent, e.g., an agent that enhances the lysis of a bacterial cell by a lysis reagent.

3.1.1 Terminology

As used herein, the terms "about" and "approximately", unless otherwise indicated, refer to a value that is no more than 20% above or below the value being modified by the term.

As used herein, the terms "agent that promotes the stabilization of the lysis reagent" and "agent that promotes the stabilization of a lysis reagent," in the context of bacteria, refer to an agent that prevents the loss of a lysis reagent's ability to lyse bacterial cells during the process of drying. In a specific embodiment, the agent prevents the loss of a lysis reagent's ability to lyse bacterial cells after exposure to temperatures of about 50° C. to about 120° C., about 50° C. to about 100° C., about 50° C. to about 85° C., about 50° C. to about 80° C., or about 60° C. to about 75° C. In another specific embodiment, the agent prevents the loss of a lysis reagent's ability to lyse bacterial cells after exposure to temperatures of about 50° C. to about 120° C., about 50° C. to about 100° C., about 50° C. to about 85° C., about 50° C. to about 80° C., or about 60° C. to about 75° C. for at least 5 minutes, at least 10 minutes, at least 15 minutes, at least 20 minutes, at least 30 minutes, at least 45 minutes, at least 1 hour, at least 1.5 hours or at least 2 hours. In another specific embodiment, the agent prevents the loss of a lysis reagent's ability to lyse bacterial cells after exposure to temperatures of about 50° C. to about 120° C., about 50° C. to about 100° C., about 50° C. to about 85° C., about 50° C. to about 80° C., or about 60° C. to about 75° C. for about 2 minutes to about 3 hours, about 2 minutes to about 2 hours, about 2 minutes to about 1 hour, about 2 minutes to about 30 minutes, about 2 minutes to about 15 minutes, about 15 minutes to about 2 hours, about 15 minutes to about 1.5 hours, about 15 minutes to about 1 hour, about 15 minutes to about 45 minutes or about 15 minutes to about 30 minutes.

As used herein, the terms "agent that promotes the stabilization of the lysis reagent" and "agent that promotes the stabilization of a lysis reagent," in the context of a microorganism, refer to an agent that prevents the loss of a lysis reagent's ability to lyse microbes during the process of drying. In a specific embodiment, the agent prevents the loss of a lysis reagent's ability to lyse microbes after exposure to temperatures of about 50° C. to about 120° C., about 50° C. to about 100° C., about 50° C. to about 85° C., about 50° C. to about 80° C., or about 60° C. to about 75° C. In another specific embodiment, the agent prevents the loss of a lysis reagent's ability to lyse microbes after exposure to temperatures of about 50° C. to about 120° C., about 50° C. to about 100° C., about 50° C. to about 85° C., about 50° C. to about 80° C., or about 60° C. to about 75° C. for at least 5 minutes, at least 10 minutes, at least 15 minutes, at least 20 minutes, at least 30 minutes, at least 45 minutes, at least 1 hour, at least 1.5 hours or at least 2 hours. In another specific embodiment, the agent prevents the loss of a lysis reagent's ability to lyse microbes after exposure to temperatures of about 50° C. to about 120° C., about 50° C. to about 100° C., about 50° C. to about 85° C., about 50° C. to about 80° C., or about 60° C. to about 75° C. for about 2 minutes to about 3 hours, about 2 minutes to about 2 hours, about 2 minutes to about 1 hour, about 2 minutes to about 30 minutes, about 2 minutes to about 15 minutes, about 15 minutes to about 2 hours, about 15 minutes to about 1.5 hours, about 15 minutes to about 1 hour, about 15 minutes to about 45 minutes or about 15 minutes to about 30 minutes.

As used herein, the term "bacterial source" refers to any source that a bacterial sample may be isolated, obtained or derived from.

As used herein, the term "intracellular bacterial target" refers to a molecule expressed, located or found inside a bacterial cell, e.g., proteins, peptides, lipids, fatty acids, metabolites, DNA and RNA. In a specific embodiment, an intracellular bacterial target is an intracellular bacterial enzyme. Non-limiting examples of intracellular bacterial enzymes include beta-lactamases, peptidases, esterases, glucose oxidase, beta-glucosidase, and glucuronidase. In certain embodiments, the intracellular bacterial enzyme is not a beta-lactamase.

As used herein, the term "intracellular bacterial target detection reagent" refers to a composition that is used in the detection of an intracellular bacterial target.

As used herein, the term "intracellular microorganism target" refers to a molecule expressed, located or found inside a microorganism, e.g., proteins, peptides, lipids, fatty acids, metabolites, DNA and RNA. In certain embodiments, the intracellular microorganism target is an intracellular microorganism enzyme. Non-limiting examples of intracellular microorganism enzymes include beta-lactamases, peptidases, esterases, glucose oxidase, beta-glucosidase, and glucuronidase. In specific embodiments, an intracellular microorganism target is an intracellular bacterial target. In other embodiments, an intracellular microorganism target is not an intracellular bacterial target.

As used herein, the term "intracellular microorganism target detection reagent" refers to a composition used in the detection of an intracellular microorganism target.

As used herein, the terms "microorganism" and "microbe" refer generally relate to any microscopic organism that expresses a molecule that is localized or found within the organism which is detectable in accordance with the methods described herein. In particular, microorganisms include, but are not limited to, bacteria, yeast, fungi, archae, prokaryotes, protozoa, parasites, and algae. These terms are not mutually exclusive, e.g., many protozoa are parasites and all bacteria are prokaryotes. In certain embodiments, a microorganism or microbe is a bacteria. In other embodiments, a microorganism or microbe is not a bacteria.

As used herein, the term "microorganism source" refers to any source that a microorganism sample may be isolated, obtained or derived from.

As used herein, the term "pure bacterial sample" means a sample collected from one or more bacterial colonies from the same source resulting from streaking an agar-containing medium with a biological sample containing bacteria. When the sample is from more than one colony, generally all of the colonies are from the same species.

As used herein, the term "no significant difference" means that the difference between two or more items is not statistically significant. In a specific embodiment, a difference is not statistically significant if the p value is greater than 0.1 or 0.05.

As used herein, the term "source" refers to anything which can provide a sample that can be used in one or more of the methods described herein. Sources may include, but are not limited to, any living subject, (e.g., a human or non-human animal), an element of nature (e.g., water or soil), a beverage (e.g., milk), a food product (e.g., meat or poultry), a cosmetic composition/formulation, or a pharmaceutical composition/formulation.

As used herein, the terms "subject" and "patient" are used interchangeably to refer to an animal subject. In a specific embodiment, the subject is a mammal. In another embodiment, the subject is a non-human. In a preferred embodiment, the subject is a human.

As used herein, the term "substrate utilization," in the context of an intracellular microorganism target, means the reaction of a substrate with an intracellular microorganism enzyme (e.g., the hydrolysis of a substrate by an intracellular microorganism enzyme) that is detectable.

As used herein, the term "substrate utilization," in the context of an intracellular bacterial target, means the reaction of a substrate with an intracellular bacterial enzyme (e.g., the hydrolysis of a substrate by an intracellular bacterial enzyme) that is detectable.

As used herein, the terms "utilization of an intracellular bacterial target detection reagent" and "utilization of the intracellular bacterial target detection reagent" refer to a detectable change in either a property of the intracellular bacterial target detection reagent or the intracellular bacterial target, or both. In one embodiment, the detectable change is a change in the chemical or physical nature of an intracellular bacterial target detection reagent (e.g., hydrolysis of an intracellular bacterial target detection reagent). In another embodiment, the detectable change is a change in the chemical or physical nature of an intracellular bacterial target resulting from the interaction of the intracellular bacterial target and the intracellular bacterial target detection reagent.

As used herein, the terms "utilization of an intracellular microorganism target detection reagent" and "utilization of the intracellular microorganism target detection reagent" refer to a detectable change in either a property of the intracellular microorganism target detection reagent or the intracellular microorganism target, or both. In one embodiment, the detectable change is a change in the chemical or physical nature of an intracellular microorganism target detection reagent (e.g., hydrolysis of an intracellular microorganism target detection reagent). In another embodiment, the detectable change is a change in the chemical or physical nature of an intracellular microorganism target resulting from the interaction of the intracellular microorganism target and the intracellular microorganism target detection reagent.

4. DETAILED DESCRIPTION

4.1 Solid Supports & Tablets

In one aspect, presented herein are solid supports containing a dry composition which provides reagents for lysing a microbe as well as reagents for the detection of an intracellular microorganism target. In a specific aspect, presented herein are solid supports containing a dried composition which provides reagents necessary to lyse a bacterial cell as well as reagents necessary to detect an intracellular bacterial target. In accordance with these aspects, the dry composition may be present in or on the solid supports. As used herein, the term "solid support" refers to a solid surface that a composition described herein may be dried on or in and is suitable for the detection of an intracellular microorganism target or an intracellular bacterial target in accordance with the methods presented herein. Non-limiting examples of solid supports include silica gels, resins, derivatized plastic films, glass beads, and polystyrene beads. In certain embodiments, the solid support is a well of a panel, a tray, a cassette or a plate (e.g., a microtiter plate). In specific embodiments, the solid support is a well of a Phoenix™ Panel (BD, USA), a well of a panel for the BBL™ Crystal™ Identification System (BD, USA), a Vitek® card (bioMerieux, USA), a well of a MicroScan panel (Dade Behring, USA), a tube for the API biochemical test (bioMerieux, USA), or a well of a panel for the Remel RapID™ System (Remel, USA). See, e.g., U.S. Pat. Nos. 5,922,593 and Des. 421,498 (each of which are incorporated herein by reference) for an exemplary description of panels with wells on or in which a composition described herein may be dried. In some embodiments, the solid support is a tube, e.g., a test tube or an eppendorf.

Solid supports containing a dried form of a composition described herein may be stored at any temperature at which the components of the dried composition do not lose substantial activity. For example, solid supports containing a dried form of a composition described herein may be stored at a temperature at which an enzyme that promotes bacterial cell lysis does not lose substantial activity. In particular embodiments, a component of a dried composition does not lose substantial activity if the component retains at least 75%, at least 80%, at least 85%, at least 90%, at least 95% or at least 99% of one or more, or all of its activities for a certain period of time after exposure to a temperature.

In a specific embodiment, a solid support containing a composition described herein in a dried form may be stored at about 35° C. or less, about 35° C. to about ° 4 C., about 35° C. to about 15° C., about 30° C. to about 20° C., about 20° C. to about 4° C., about 15° C. to about 4° C., or room temperature. In another specific embodiment, a solid support containing a composition described herein in a dried form may be stored at about 4° C. to about −20° C., about 4° C. to about −60° C., about 4° C. to about −70° C., or about 4° C. to about −80° C., or about −20° C. to about −80° C. In certain embodiments, a solid support containing a composition described herein in a dried form may be stored for about 1 week to about 1 month, about 1 week to about 2 months, about 1 week to about 3 months, about 1 week to about 4 months, about 1 week to about 6 months, about 1 month to 12 months or about 2 months to about 12 months at about 35° C. or less, about 35° C. to about ° 4 C., about 35° C. to about 15° C., about 30° C. to about 20° C., about 20° C. to about 4° C., about 15° C. to about 4° C., or room temperature. In some embodiments, a solid support containing a composition described herein in dried form may be stored for about 1 week to about 1 month, about 1 week to about 2 months, about 1 week to about 3 months, about 1 week to about 4 months, about 1 week to about 6 months, about 1 month to 12 months or about 2 months to about 12 months at about 4° C. to about −20° C., about 4° C. to about −60° C., about 4° C. to about −70° C., or about 4° C. to about −80° C., or about −20° C. to about −80° C.

In another aspect, presented herein are dry powders comprising reagents necessary to lyse a microbe as well as reagents necessary to detect an intracellular microorganism target. In a specific aspect, presented herein are dry powders comprising reagents necessary to lyse a bacterial cell as well as reagents necessary to detect an intracellular bacterial target. Such dry powders may be stored at any temperature at which the components of the composition do not substantial lose activity. In a specific embodiment, the dry powders may be stored at about 35° C. or less, about 35° C. to about ° 4 C., about 35° C. to about 15° C., about 30° C. to about 20° C., about 20° C. to about 4° C., about 15° C. to about 4° C., or room temperature. In another specific embodiment, the dry powders may be stored at about 4° C. to about −20° C., about 4° C. to about −60° C., about 4° C. to about −70° C., or about 4° C. to about −80° C., or about −20° C. to about −80° C. In certain embodiments, the dry powders may be stored for about 1 week to about 1 month, about 1 week to about 2 months, about 1 week to about 3 months, about 1 week to about 4 months, about 1 week to about 6 months, about 1 month to 12 months or about 2 months to about 12 months at about 35° C. or less, about 35° C. to about ° 4 C., about 35° C. to about 15° C., about 30° C. to about 20° C., about 20° C. to about 4° C., about 15° C. to about 4° C., or room temperature. In some embodiments, the dry powders may be stored for about 1 week to about 1 month, about 1 week to about 2 months, about 1 week to about 3 months, about 1 week to about 4 months, about 1 week to about 6 months, about 1 month to 12 months or about 2 months to about 12 months at about 4° C. to about −20° C., about 4° C. to about −60° C., about 4° C. to about −70° C., or about 4° C. to about −80° C., or about −20° C. to about −80° C.

In another aspect, presented herein are tablets comprising a composition which provides reagents necessary to lyse a microbe as well as reagents necessary to detect an intracellular microorganism target. In a specific aspect, presented herein are tablets comprising a composition which provides reagents necessary to lyse a bacterial cell as well as reagents necessary to detect an intracellular bacterial target. Tablets comprising a composition described herein may be stored at any temperature at which the components of the composition do not substantial lose activity. In a specific embodiment, a tablet comprising a composition described herein may be stored at about 35° C. or less, about 35° C. to about ° 4 C., about 35° C. to about 15° C., about 30° C. to about 20° C., about 20° C. to about 4° C., about 15° C. to about 4° C., or room temperature. In another specific embodiment, a tablet comprising a composition described herein may be stored at about 4° C. to about −20° C., about 4° C. to about −60° C., about 4° C. to about −70° C., or about 4° C. to about −80° C., or about −20° C. to about −80° C. In certain embodiments, a tablet comprising a composition may be stored for about 1 week to about 1 month, about 1 week to about 2 months, about 1 week to about 3 months, about 1 week to about 4 months, about 1 week to about 6 months, about 1 month to 12 months or about 2 months to about 12 months at about 35° C. or less, about 35° C. to about ° 4 C., about 35° C. to about 15° C., about 30° C. to about 20° C., about 20° C. to about 4° C., about 15° C. to about 4° C., or room temperature. In some embodiments, a tablet comprising a composition described herein may be stored for about 1 week to about 1 month, about 1 week to about 2 months, about 1 week to about 3 months, about 1 week to about 4 months, about 1 week to about 6 months, about 1 month to 12 months or about 2 months to about 12 months at about 4° C. to about −20° C., about 4° C. to about −60° C., about 4° C. to about −70° C., or about 4° C. to about −80° C., or about −20° C. to about −80° C.

4.2 Compositions 4.2.1 Compositions for Detecting an Intracellular Microorganism Targets In an aspect, presented herein are compositions which provides reagents for lysing a microorganism and reagents for detection of an intracellular microorganism target. In one embodiment, presented herein are compositions comprising reagents necessary to lyse a microbe as well as reagents necessary to detect an intracellular microorganism target. In a specific embodiment, a composition comprises a lysis reagent and one or more intracellular microorganism target detection reagents. Lysis reagents are known to one of skill in the art. In certain embodiments, the type of microorganism and the host for the microorganism is considered when selecting the lysis reagent. For example, if the microorganism is an intracellular parasite, then a lysis reagent can be selected that not only lyses the parasite but also the cells in which the parasite is found. In a specific embodiment, the lysis reagent lyses the microbe but does not substantially interfere with the ability of the intracellular microorganism target to be detected. Lysis reagents that do not substantially interfere with the ability of an intracellular microorganism target to be detected may be identified by, e.g., comparing the utilization of an intracellular microorganism target detection reagent in the presence and absence of a lysis reagent, wherein a lysis reagent that does not substantially interfere with the ability of the intracellular microorganism target to be detected is identified if there is no significant difference between the utilization of the intracellular microorganism target detection reagent in the absence and presence of the lysis reagent. Lysis reagents that do not substantially interfere with the ability of an intracellular microorganism target to be detected may also be identified if, e.g., the utilization of an intracellular microorganism target detection reagent in the presence of the lysis reagent is about the same or better than a pre-determined threshold level of utilization of the intracellular microorganism target detection reagent.

In one embodiment, the lysis reagent is a detergent, such as a mild non-denaturing detergent (e.g., Triton® X-100 or CHAPS). In another embodiment, the lysis reagent is an enzyme or other agent that promotes the lysis of a microbe. Non-limiting examples of such an enzyme include lysozyme, labiase, lysostaphin, achromopeptidase, and mutanolysin. In a particular embodiment, in a composition described herein, an enzyme or other agent that promotes the lysis of a microbe is about 5% to about 30%, about 5% to about 25%, about 5% to about 20%, about 5% to about 15%, or about 5% to about 10% by weight of the total weight of the composition. In another embodiment, in a composition described herein, an enzyme or other agent that promotes the lysis of a microbe is about 10% to about 30%, about 10% to about 25%, about 10% to about 20%, or about 10% to about 15% by weight of the total weight of the composition. In another embodiment, in a composition described herein, an enzyme or other agent that promotes lysis of a microbe is about 5%, about 10%, about 15%, about 20%, about 25% or about 30% by weight of the total weight of the composition.

In another embodiment, an enzyme or other agent that promotes the lysis of a microbe is present in a composition described herein at a concentration of about 0.1 mg/ml to about 100 mg/ml, about 1 mg/ml to about 100 mg/ml, about 10 mg/ml to about 100 mg/ml, about 25 mg/ml to about 100 mg/ml, about 50 mg/ml to about 100 mg/ml, about 75 mg/ml to about 100 mg/ml or about 85 mg/ml to about 100 mg/ml after rehydration. In another embodiment, an enzyme or other agent that promotes the lysis of a microbe is present in a composition described herein at a concentration of about 10 mg/ml to about 75 mg/ml, about 10 mg/ml to about 60 mg/ml, about 10 mg/ml to about 50 mg/ml, about 10 mg/ml to about 40 mg/ml, about 10 mg/ml to about 30 mg/ml, about 10 mg/ml to about 25 mg/ml or about 10 mg/ml to about 15 mg/ml after rehydration. In another embodiment, an enzyme or other agent that promotes the lysis of a microbe is present in a composition described herein at a concentration of about 10 mg/ml, about 15 mg/ml, about 25 mg/ml, about 30 mg/ml, about 40 mg/ml, about 50 mg/ml, about 60 mg/ml, about 70 mg/ml, about 75 mg/ml, about 80 mg/ml, about 90 mg/ml, or about 100 mg/ml after rehydration.

In another embodiment, an enzyme or other agent that promotes the lysis of a microbe is present in a composition described herein at a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml after rehydration. In another embodiment, an enzyme or other agent that promotes the lysis of a microbe is present in a composition described herein at a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml after rehydration.

In certain embodiments, a composition comprises a lysis reagent, an agent that promotes the stabilization of the lysis reagent, and one or more intracellular microorganism target detection reagents. In a specific embodiment, the agent that promotes the stabilization of the lysis reagent does not substantially interfere with the ability of the intracellular microorganism target to be detected. Agents that do not substantially interfere with the ability of the intracellular microorganism target to be detected may be identified by, e.g., comparing the utilization of an intracellular microorganism target detection reagent in the presence and absence of an agent that promotes the stabilization of a lysis reagent, wherein an agent that promotes the stabilization of a lysis buffer which does not substantially interfere with the ability of the intracellular microorganism target to be detected is identified if there is no significant difference in the utilization of the intracellular microorganism target detection reagent in the presence and absence of the agent. Agents that do not substantially interfere with the ability of an intracellular microorganism target to be detected may also be identified if, e.g., the utilization of an intracellular microorganism target detection reagent in the presence of the agent is about the same or better than a pre-determined threshold level of utilization of the intracellular microorganism target detection reagent.

In one embodiment, the agent that promotes the stabilization of the lysis reagent is thermal stable. In a specific embodiment, the agent that promotes the stabilization of the lysis reagent is stable at temperatures of about 60° C. or higher, about 50° C. to about 100° C., about 60° C. to about 90° C., about 60° C. to about 85° C., about 60° C. to about 75° C., or about 60° C. to about 70° C. In a particular embodiment, in a composition described herein, an agent that promotes stabilization of the lysis reagent is about 0.1% to about 70%, about 1% to about 70%, about 10% to about 60%, about 10% to about 50%, about 10% to about 40%, about 10% to about 30%, about 10% to about 25%, or about 10% to about 15% by weight of the total weight of the composition. In another embodiment, in a composition described herein, an agent that promotes stabilization of the lysis reagent is about 20% to about 70%, about 20% to about 65%, about 20% to about 60%, about 20% to about 50%, about 20% to about 40%, about 20% to about 30%, or about 20% to about 25% by weight of the total weight of the composition. In another embodiment, in a composition described herein, an agent that promotes stabilization of the lysis reagent is about 20%, about 30%, about 40%, about 50%, about 60%, about 65%, about 66%, or about 70% by weight of the total weight of the composition.

In another embodiment, an agent that promotes stabilization of the lysis reagent is present in a composition described herein at a concentration of about 0.1 mg/ml to about 100 mg/ml, about 1 mg/ml to about 100 mg/ml, about 10 mg/ml to about 100 mg/ml, about 25 mg/ml to about 100 mg/ml, about 50 mg/ml to about 100 mg/ml, about 75 mg/ml to about 100 mg/ml or about 85 mg/ml to about 100 mg/ml after rehydration. In another embodiment, an agent that promotes stabilization of the lysis reagent is present in a composition described herein at a concentration of about 10 mg/ml to about 75 mg/ml, about 10 mg/ml to about 60 mg/ml, about 10 mg/ml to about 50 mg/ml, about 10 mg/ml to about 40 mg/ml, about 10 mg/ml to about 30 mg/ml, about 10 mg/ml to about 25 mg/ml or about 10 mg/ml to about 15 mg/ml after rehydration. In another embodiment, an agent that promotes stabilization of the lysis reagent is present in a composition described herein at a concentration of about 10 mg/ml, about 15 mg/ml, about 25 mg/ml, about 30 mg/ml, about 40 mg/ml, about 50 mg/ml, about 60 mg/ml, about 70 mg/ml, about 75 mg/ml, about 80 mg/ml, about 90 mg/ml, or about 100 mg/ml after rehydration.

In certain embodiments, a composition comprises a lysis reagent, an agent that promotes the stabilization of the lysis reagent, an agent that enhances the lysis of a microorganism cell by a lysis reagent (e.g., a metal chelator), and one or more intracellular microorganism target detection reagents. In a specific embodiment, the agent that enhances the lysis of a microbe by a lysis reagent does not substantially interfere with the ability of the intracellular microorganism target to be detected. Agents that do not substantially interfere with the ability of the intracellular microorganism target to be detected may be identified by, e.g., comparing the utilization of an intracellular microorganism target detection reagent in the presence and absence of an agent that enhances the lysis of a microorganism by a lysis reagent, wherein an agent that enhances the lysis of a microorganism by a lysis reagent which does not substantially interfere with the ability of the intracellular microorganism target to be detected is identified if there is no significant difference in the utilization of the intracellular microorganism target detection reagent in the presence and absence of the agent. Agents that do not substantially interfere with the ability of an intracellular microorganism target to be detected may also be identified if, e.g., the utilization of an intracellular microorganism target detection reagent in the presence of the agent is about the same or better than a pre-determined threshold level of utilization of the intracellular microorganism target detection reagent.

In specific embodiments, an agent that enhances the lysis of a microbe by a lysis reagent increases the rate at which the lysis reagent lyses microbes by about 10%, about 20%, about 25%, about 30%, about 40%, about 50%, about 60% or about 75% relative the rate at which the lysis reagent lyses microbes in the absence of the agent. In other embodiments, an agent that enhances the lysis of a microbe by a lysis reagent the increases rate at which the lysis reagent lyses microbes by about 10% to about 50%, about 10% to about 75%, about 25% to about 75%, about 25% to about 50%, about 25% to about 40%, about 25% to about 30% or about 50% or about 75% relative the rate at which the lysis reagent lyses microbes in the absence of the agent.

In specific embodiments, an agent that enhances the lysis of a microbe by a lysis reagent increases the efficiency of the lysis of microbes by the lysis reagent by about 10%, about 20%, about 25%, about 30%, about 40%, about 50%, about 60% or about 75% relative the efficiency of the lysis of microbes by the lysis reagent in the absence of the agent. In other embodiments, an agent that enhances the lysis of a microbe by a lysis reagent the increases the efficiency of the lysis of microbes by the lysis reagent by about 10% to about 50%, about 10% to about 75%, about 25% to about 75%, about 25% to about 50%, about 25% to about 40%, about 25% to about 30% or about 50% or about 75% relative the efficiency of the lysis of microbes by the lysis reagent in the absence of the agent. The efficiency of the lysis of microbes by a lysis reagent can be determined by, e.g., measuring the percentage or number of microbes lysed by a lysis reagent using techniques known to one skilled in the art.

In one embodiment, in a composition described herein, an agent that enhances the lysis of a microbe by a lysis reagent is about 1% to about 20%, about 5% to about 20%, about 10% to about 20%, or about 15% to about 20% by weight of the total weight of the composition. In another embodiment, in a composition described herein, an agent that enhances the lysis of a microbe by a lysis reagent is about 1%, about 5%, about 8%, about 10%, about 15%, or about 20% by weight of the total weight of the composition.

In another embodiment, a composition comprises an agent that enhances the lysis of a microbe by a lysis reagent is present in a composition described herein at a concentration of about 0.01 mM to about 10 mM, about 0.05 mM to about 10 mM, about 0.1 mM to about 10 mM, about 0.5 mM to about 10 mM, about 1 mM to about 10 mM, about 2 mM to about 10 mM, about 5 mM to about 10 mM, or about 8 to about 10 mM after rehydration. In another embodiment, a composition comprises an agent that enhances the lysis of a microbe by a lysis reagent is present in a composition described herein at a concentration of about 0.01 mM to about 5 mM, about 0.05 mM to about 5 mM, about 0.1 mM to about 5 mM, about 1 mM to about 4 mM, about 1 mM to about 3 mM, about 2 mM to about 3 mM, about 0.1 mM to about 2 mM, or about 0.01 mM to about 1 mM after rehydration. In another embodiment, a composition comprises an agent that enhances the lysis of a microbe by a lysis reagent is present in a composition described herein at a concentration of about 0.01 mM, about 0.05 mM, about 0.1 mM, about 0.5 mM, about 1 mM, about 2 mM, about 3 mM, about 4 mM, about 5 mM, about 6 mM, about 7 mM, about 8 mM, about 9 mM, or about 10 mM after rehydration.

In some embodiments, the compositions described herein may include a buffer(s). Any buffer that aids in maintaining the pH of the composition and does not interfere with the ability of an intracellular microorganism target to be detected may be used. Non-limiting examples of buffers include phosphate MES buffer, acetate buffer, Tris buffer, ADA buffer, MDPS buffer, and HEPES buffer. In an embodiment, a composition described herein is about pH 5 to about pH 8, preferably about pH 5.5 to about pH 7.5, and more preferably pH 6 to about pH 7.

In one embodiment, in a composition described herein, a buffer is about 1% to about 10%, about 1% to about 10%, about 8% to about 10%, about 5% to about 10%, or about 2% to about 10% by weight of the total weight of the composition. In another embodiment, in a composition described herein, buffer is about 1%, about 2%, about 3%, about 4%, about 5%, about 6%, about 7%, about 8%, about 9% or about 10% by weight of the total weight of the composition.

In another embodiment, a composition comprises about 10 mM to about 200 mM, about 25 mM to about 200 mM, about 50 mM to about 200 mM, about 75 mM to about 200 mM, about 100 mM to about 200 mM, about 125 mM to about 200 mM, about 150 mM to about 200 mM, or about 175 mM to about 200 mM of a buffer (e.g., phosphate or MES buffer) after rehydration. In another embodiment, a composition comprises about 10 mM, about 25 mM, about 50 mM, about 75 mM, about 100 mM, about 125 mM, about 150 mM, about 175 mM, or about 200 mM of a buffer (e.g., phosphate or MES buffer) after rehydration.

In some embodiments, a composition described herein may comprise an agent that assists with the identification of a particular class, type or subtype of a particular intracellular microorganism target.

Intracellular microorganism target detection reagents for use in the detection of intracellular microorganism targets are known to those skilled in the art. In some embodiments, the intracellular microorganism target detection reagent is membrane impermeable. In other embodiments, the intracellular microorganism target detection reagent is membrane permeable. In some embodiments, the presence of a lysis reagent increases the rate of utilization of an intracellular microorganism target detection reagent by an intracellular bacterial target. In one embodiment, the intracellular microorganism target detection reagent is a substrate for an intracellular microorganism target. For example, the intracellular microorganism target detection reagent is a substrate that the intracellular microorganism target hydrolyzes. In another embodiment, the intracellular microorganism target detection reagent forms a complex with an intracellular microorganism target which is detectable. In certain embodiments, a composition described herein is dried on or in a solid support and comprises two or more intracellular microorganism target detection reagents. In some embodiments, the presence of two or more intracellular microorganism target detection reagents allows for the detection of two or more intracellular microorganism targets.

Although the compositions described herein are with respect to intracellular microorganism targets, the compositions may include, in addition to or in place of an intracellular microorganism target detection reagent, reagents necessary for the detection of a microorganism target (e.g., protein, peptide, lipid, carbohydrate, or fatty acid) that is expressed, present or located on the surface of a microorganism. One skilled in the art would know what reagents could be used to detect microorganism targets expressed, present or located on the cell surface.

In some embodiments, a composition described herein is filtered using, e.g., a 0.2 micron filter. A composition described herein may or may not be filtered prior to drying the composition. In certain embodiments, a composition described herein is subjected to gamma irradiation, or is autoclaved. A composition described herein may or may not subjected to gamma irradiation or autoclaved before drying the composition. In other embodiments, a composition described herein is not subjected to any process that adversely affects the activity of one or more of the components of the composition (e.g., an enzyme that promotes the lysis of a microbe). In specific embodiments, a composition described herein is not subjected to gamma irradiation, or is not autoclaved.

In some embodiments, a composition described herein is dried on or in a solid support using heat at temperatures of, e.g., about 50° C. to about 100° C., about 50° C. to about 85° C., about 50° C. to about 75° C., about 60° C. to about 75° C., or about 60° C. to about 70° C. In one embodiment, a composition described herein is dried on or in a solid support using heat under forced air or vacuum conditions at temperatures of, e.g., about 50° C. to about 100° C., about 50° C. to about 85° C., about 50° C. to about 75° C., about 60° C. to about 75° C., or about 60° C. to about 70° C. In other embodiments, a composition described herein is dried on or in a solid support using a lypholization technique. In other embodiments, a composition described herein is dried on or in a solid support using a spray drying technique.

In one embodiment, a composition described herein is dried and is present in or on a paper disk or paper strip. In certain embodiments, a paper disk or paper strip is divided up into different sections with each section having a different dried composition. For example, the paper disk or paper strip may comprise three sections with each section comprising a different dried composition comprising an intracellular microorganism target detection reagent and a lysis reagent. In another embodiment, there is only one composition per paper disk or paper strip. In other words, each paper disk or paper strip only comprises one dried composition. In a specific embodiment, the paper disk or paper strip is filter paper. In another specific embodiment, a composition presented herein dried and is present in a BBL™ Dryslide™ Nitrocefin (Becton Dickinson, Diagnostic Systems, USA), or a solid support similar to a BBL™ Dryslide™ Nitrocefin (Becton Dickinson, Diagnostic Systems, USA).

In certain embodiments, a composition described herein is dried and present in a well of a panel, a tray, a cassette or a plate (e.g., a microtiter plate). In some embodiments, different wells of a panel, a tray, a cassette or a plate contain a different dried composition. In specific embodiments, a composition described herein is dried and is present in a well of a tray, a panel, a tray or a cassette using, e.g., heat.

In certain embodiments, a composition described herein is dried and is present in a tube, e.g., a test tube or eppendorf. In some embodiments, a composition described herein is in the form of a dry powder. In certain embodiments, a composition described herein is used to form a tablet.

4.2.2 Compositions for Detecting an Intracellular Bacterial Target

In a specific aspect, presented herein are compositions comprising reagents necessary to lyse a bacterial cell as well as reagents necessary to detect an intracellular bacterial target. In a specific embodiment, a composition comprises a lysis reagent and one or more intracellular bacterial target detection reagents. Lysis reagents are known to one of skill in the art. In certain embodiments, the type of bacteria and the host of the bacteria is considered when selecting the lysis reagent. For example, if the bacteria is an intracellular bacteria (e.g., *Mycobacterium tuberculosis*), then a lysis reagent can be selected that not only lyses the bacteria but also the cells in which the bacteria is found. In a specific embodiment, the lysis reagent lyses the bacterial cells but does not substantially interfere with the ability of the intracellular bacterial target to be detected. Lysis reagents that do not substantially interfere with the ability of an intracellular bacterial target to be detected may be identified by, e.g., comparing the utilization of an intracellular bacterial target detection reagent in the presence and absence of a lysis reagent, wherein a lysis reagent that does not substantially interfere with the ability of the intracellular bacterial target to be detected is identified if there is no significant difference between the utilization of the intracellular bacterial target detection reagent in the absence and presence of the lysis reagent. Lysis reagents that do not substantially interfere with the ability of an intracellular bacterial target to be detected may also be identified if, e.g., the utilization of an intracellular bacterial target detection reagent in the presence of the lysis reagent is about the same or better than a pre-determined threshold level of utilization of the intracellular bacterial target detection reagent.

In one embodiment, the lysis reagent is a detergent, such as a mild non-denaturing detergent (e.g., Triton® X-100 or CHAPS). In another embodiment, the lysis reagent is an enzyme or other agent that promotes the lysis of a bacterial cell. Non-limiting examples of such an enzyme include lysozyme, labiase, lysostaphin, achromopeptidase, and mutanolysin. In a particular embodiment, in a composition described herein, an enzyme or other agent that promotes the lysis of a bacterial cell is about 5% to about 30%, about 5% to about 25%, about 5% to about 20%, about 5% to about 15%, or about 5% to about 10% by weight of the total weight of the composition. In another embodiment, in a composition described herein, an enzyme or other agent that promotes the lysis of a bacterial cell is about 10% to about 30%, about 10% to about 25%, about 10% to about 20%, or about 10% to about 15% by weight of the total weight of the composition. In another embodiment, in a composition described herein, an enzyme or other agent that promotes lysis of a bacterial is about 5%, about 10%, about 15%, about 20%, about 25% or about 30% by weight of the total weight of the composition.

In another embodiment, an enzyme or other agent that promotes the lysis of a bacterial cell is present in a composition described herein at a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml. In another embodiment, an enzyme or other agent that promotes the lysis of a bacterial cell is present in a composition described herein at a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml.

In another embodiment, an enzyme or other agent that promotes the lysis of a bacterial cell is present in a composition described herein at a concentration of about 0.1 mg/ml to about 100 mg/ml, about 1 mg/ml to about 100 mg/ml, about 10 mg/ml to about 100 mg/ml, about 25 mg/ml to about 100 mg/ml, about 50 mg/ml to about 100 mg/ml, about 75 mg/ml to about 100 mg/ml or about 85 mg/ml to about 100 mg/ml after rehydration. In another embodiment, an enzyme or other agent that promotes the lysis of a bacterial cell is present in a composition described herein at a concentration of about 10 mg/ml to about 75 mg/ml, about 10 mg/ml to about 60 mg/ml, about 10 mg/ml to about 50 mg/ml, about 10 mg/ml to about 40 mg/ml, about 10 mg/ml to about 30 mg/ml, about 10 mg/ml to about 25 mg/ml or about 10 mg/ml to about 15 mg/ml after rehydration. In another embodiment, an enzyme or other agent that promotes the lysis of a bacterial cell is present in a composition described herein at a concentration of about 10 mg/ml, about 15 mg/ml, about 25 mg/ml, about 30 mg/ml, about 40 mg/ml, about 50 mg/ml, about 60 mg/ml, about 70 mg/ml, about 75 mg/ml, about 80 mg/ml, about 90 mg/ml, or about 100 mg/ml after rehydration.

In another embodiment, an enzyme or other agent that promotes the lysis of a bacterial cell is present in a composition described herein at a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml after rehydration. In another embodiment, an enzyme or other agent that promotes the lysis of a bacterial cell is present in a composition described herein at a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml after rehydration.

In a specific embodiment, a composition comprises lysozyme and one or more intracellular bacterial target detection reagents. In a particular embodiment, a composition described herein comprises: (i) about 5% to about 30% of lysozyme by weight of the total weight of the composition, about 5% to about 25% of lysozyme by weight of the total weight of the composition, about 5% to about 20% of lysozyme by weight of the total weight of the composition, about 5% to about 15% of lysozyme by weight of the total weight of the composition, or about 5% to about 10% of lysozyme by weight of the total weight of the composition; and (ii) one or more intracellular bacterial target detection reagents. In another embodiment, a composition described herein comprises lysozyme at a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/m) to about 10 mg/ml and one or more intracellular detection reagents. In another embodiment, a composition described herein comprises lysozyme at a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml and one or more intracellular bacterial target detection reagents.

In another embodiment, a composition described herein comprises: (i) lysozyme at a concentration of about 10 mg/ml to about 100 mg/ml, about 20 mg/ml to about 100 mg/ml, about 30 mg/ml to about 100 mg/ml, about 40 mg/ml to about 100 mg/ml, about 50 mg/ml to about 100 mg/ml, about 60 mg/ml to about 100 mg/ml, about 70 mg/ml to about 100 mg/ml, about 80 mg/ml to about 100 mg/ml, about 90 mg/ml to about 100 mg/ml or about 5 mg/ml to about 10 mg/ml after rehydration; and (ii) one or more intracellular bacterial target detection reagents. In another embodiment, a composition described herein comprises; (i) lysozyme at a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mWm1 to about 10 mg/ml or about 5 mg/ml to about 10 mg/ml after rehydration; and (ii) one or more intracellular bacterial target detection reagents. In another embodiment, a composition described herein comprises: (i) lysozyme at a concentration of about 0.1 mg/ml to about 8 mg/ml, about 1 mg/ml to about 6 mg/ml, about 1 mg/ml to about 5 mg/ml, about 1 mg/ml to about 4 mg/ml, about 2 mg/ml to 4 mg/ml, or about 3 mg/ml after rehydration; and (ii) one or more intracellular bacterial target detection reagents.

In certain embodiments, a composition comprises a lysis reagent (e.g., lysozyme, labiase, lysostaphin, achromopeptidase, or mutanolysin), an agent that promotes the stabilization of the lysis reagent, and one or more intracellular bacterial target detection reagents. In a specific embodiment, the agent that promotes the stabilization of the lysis reagent does not substantially interfere with the ability of the intracellular bacterial target to be detected. Agents that do not substantially interfere with the ability of the intracellular bacterial target to be detected may be identified by, e.g., comparing the utilization of an intracellular bacterial target detection reagent in the presence and absence of an agent that promotes the stabilization of a lysis reagent, wherein an agent that promotes the stabilization of a lysis buffer which does not substantially interfere with the ability of the intracellular bacterial target to be detected is identified if there is no significant difference in the utilization of the intracellular bacterial target detection reagent in the presence and absence of the agent. Agents that do not substantially interfere with the ability of an intracellular bacterial target to be detected may also be identified if, e.g., the utilization of an intracellular bacterial target detection reagent in the presence of the agent is about the same or better than a pre-determined threshold level of utilization of the intracellular bacterial target detection reagent. In one embodiment, the agent that promotes the stabilization of the lysis reagent is thermal stable. In a specific embodiment, the agent that promotes the stabilization of the lysis reagent is stable at temperatures of about 60° C. or higher, about 50° C. to about 100° C., about 60° C. to about 90° C., about 60° C. to about 85° C., about 60° C. to about 75° C., or about 60° C. to about 70° C.

In a particular embodiment, in a composition described herein, an agent that promotes stabilization of the lysis reagent is about 0.1% to about 70%, about 1% to about 70%, about 10% to about 60%, about 10% to about 50%, about 10% to about 40%, about 10% to about 30%, about 10% to about 25%, or about 10% to about 15% by weight of the total weight of the composition. In another embodiment, in a composition described herein, an agent that promotes stabilization of the lysis reagent is about 20% to about 70%, about 20% to about 65%, about 20% to about 60%, about 20% to about 50%, about 20% to about 40%, about 20% to about 30%, or about 20% to about 25% by weight of the total weight of the composition. In another embodiment, in a composition described herein, an agent that promotes stabilization of the lysis reagent is about 20%, about 30%, about 40%, about 50%, about 60%, about 65% or about 70% by weight of the total weight of the composition. In another embodiment, a composition comprises a concentration of about 0.1% to about 10%, about 1% to about 10%, about 2% to about 10%, about 4% to about 10%, about 1% to about 8%, about 2% to about 8%, about 2% to about 6%, or about 2% to about 4% of an agent that promotes the stabilization of the lysis reagent. In another embodiment, a composition comprises a concentration of about 0.1% to about 10%, about 1% to about 10%, about 2% to about 10%, about 4% to about 10%, about 1% to about 8%, about 2% to about 8%, about 2% to about 6%, or about 2% to about 4% of an agent that promotes the stabilization of the lysis reagent after rehydration.

In another embodiment, an agent that promotes stabilization of the lysis reagent is present in a composition described herein at a concentration of about 0.1 mg/ml to about 100 mg/ml, about 1 mg/ml to about 100 mg/ml, about 10 mg/ml to about 100 mg/ml, about 25 mg/ml to about 100 mg/ml, about 50 mg/ml to about 100 mg/ml, about 75 mg/ml to about 100 mg/ml or about 85 mg/ml to about 100 mg/ml after rehydration. In another embodiment, an agent that promotes stabilization of the lysis reagent is present in a composition described herein at a concentration of about 10 mg/ml to about 75 mg/ml, about 10 mg/ml to about 60 mg/ml, about 10 mg/ml to about 50 mg/ml, about 10 mg/ml to about 40 mg/ml, about 10 mg/ml to about 30 mg/ml, about 10 mg/ml to about 25 mg/ml or about 10 mg/ml to about 15 mg/ml after rehydration. In another embodiment, an agent that promotes stabilization of the lysis reagent is present in a composition described herein at a concentration of about 10 mg/ml, about 15 mg/ml, about 25 mg/ml, about 30 mg/ml, about 40 mg/ml, about 50 mg/ml, about 60 mg/ml, about 70 mg/ml, about 75 mg/ml, about 80 mg/ml, about 90 mg/ml, or about 100 mg/ml after rehydration.

In a specific embodiment, a composition comprises a lysis reagent (e.g., lysozyme, labiase, lysostaphin, achromopeptidase, or mutanolysin), a carbohydrate (e.g., a monosaccharide, a disaccharide, a polysaccharide, an oligosaccharide, or a polyol), and one or more intracellular bacterial target detection reagents. Specific examples of carbohydrates include, but are not limited to, mannitol, ribose, glucose, fructose, mannose, sucrose, lactose, glycerol, Xanthan gum, trehalose and glycols (e.g., propylene glycol). In a specific embodiment, the carbohydrate is trehalose.

In a specific embodiment, a composition comprises lysozyme, trehalose and one or more intracellular bacterial target detection reagents. In a particular embodiment, a composition described herein comprises: (i) about 5% to about 30% of lysozyme by weight of the total weight of the composition, about 5% to about 25% of lysozyme by weight of the total weight of the composition, about 5% to about 20% of lysozyme by weight of the total weight of the composition, about 5% to about 15% of lysozyme by weight of the total weight of the composition, or about 5% to about 10% of lysozyme by weight of the total weight of the composition; (ii) about 20% to about 70% of trehalose by weight of the total weight of the composition, about 20% to about 65% of trehalose by weight of the total weight of the composition, about 20% to about 60% of trehalose by weight of the total weight of the composition, about 20% to about 50% of trehalose by weight of the total weight of the composition, about 20% to about 40% of trehalose by weight of the total weight of the composition, about 20% to about 30% of trehalose by weight of the total weight of the composition, or about 20% to about 25% of trehalose by weight of the total weight of the composition; and (iii) one or more intracellular bacterial target detection reagents. In another embodiment, a composition described herein comprises: (i) a concentration of about 10 mg/ml to about 100 mg/ml, about 10 mg/ml to about 75 mg/ml, about 10 mg/ml to about 60 mg/ml, about 10 mg/ml to about 50 mg/ml, about 10 mg/ml to about 40 mg/ml, about 10 mg/ml to about 30 mg/ml, about 10 mg/ml to about 25 mg/ml or about 10 mg/ml to about 15 mg/ml of lysozyme after rehydration; (ii) a concentration of about 10 mg/ml to about 100 mg/ml, about 25 mg/ml to about 100 mg/ml, about 50 mg/ml to about 100 mg/ml, about 75 mg/ml to about 100 mg/ml or about 85 mg/ml to about 100 mg/ml of trehalose after rehydration; and (iii) one or more intracellular bacterial target detection reagents.

In another embodiment, a composition described herein comprises: (i) a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme after rehydration; (ii) about 0.1% to about 10%, about 1% to about 10%, about 2% to about 10%, about 4% to about 10%, about 1% to about 8%, about 2% to about 8%, about 2% to about 6%, or about 2% to about 4% of trehalose by weight of the total weight of the composition; and (iii) one or more intracellular bacterial target detection reagents. In another embodiment, a composition described herein comprises: (i) a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme after rehydration; (ii) about 0.1% to about 10%, about 1% to about 10%, about 2% to about 10%, about 4% to about 10%, about 1% to about 8%, about 2% to about 8%, about 2% to about 6%, or about 2% to about 4% of trehalose by weight of the total weight of the composition; and (iii) one or more intracellular bacterial target detection reagents.

In another embodiment, a composition described herein comprises a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme after rehydration, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose after rehydration, and one or more intracellular bacterial target detection reagents. In another embodiment, a composition described herein comprises a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme after rehydration, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose after rehydration, and one or more intracellular bacterial target detection reagents.

In another embodiment, a composition described herein comprises a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose, and one or more intracellular bacterial target detection reagents. In another embodiment, a composition described herein comprises a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose, and one or more intracellular bacterial target detection reagents.

In certain embodiments, a composition comprises a lysis reagent (e.g., lysozyme, labiase, lysostaphin, achromopeptidase, or mutanolysin), an agent that promotes the stabilization of the lysis reagent, an agent that enhances the lysis of a bacterial cell by a lysis reagent (e.g., a metal chelator), and one or more intracellular bacterial target detection reagents. In a specific embodiment, the agent that enhances the lysis of a bacterial cell by a lysis reagent does not substantially interfere with the ability of the intracellular bacterial target to be detected. Agents that do not substantially interfere with the ability of an intracellular bacterial target to be detected may be identified by, e.g., comparing the utilization of an intracellular bacterial target detection reagent in the presence and absence of an agent that enhances the lysis of a bacterial cell by a lysis reagent, wherein an agent that enhances the lysis of a bacterial cell by a lysis buffer which does not substantially interfere with the ability of the intracellular bacterial target to be detected is identified if there is no significant difference in the utilization of the intracellular bacterial target detection reagent in the presence and absence of the agent. Agents that do not substantially interfere with the ability of an intracellular bacterial target to be detected may also be identified if, e.g., the utilization of an intracellular bacterial target detection reagent in the presence of the agent is about the same or better than a pre-determined threshold level of utilization of the intracellular bacterial target detection reagent.

In specific embodiments, an agent that enhances the lysis of a bacterial cell by a lysis reagent increases the rate at which the lysis reagent lyses bacterial cells by about 10%, about 20%, about 25%, about 30%, about 40%, about 50%, about 60% or about 75% relative the rate at which the lysis reagent lyses bacterial cells in the absence of the agent. In other embodiments, an agent that enhances the lysis of a bacterial cell by a lysis reagent the increases rate at which the lysis reagent lyses bacterial cells by about 10% to about 50%, about 10% to about 75%, about 25% to about 75%, about 25% to about 50%, about 25% to about 40%, about 25% to about 30% or about 50% or about 75% relative the rate at which the lysis reagent lyses bacterial cells in the absence of the agent.

In specific embodiments, an agent that enhances the lysis of a bacterial cell by a lysis reagent increases the efficiency of the lysis of bacterial cells by the lysis reagent by about 10%, about 20%, about 25%, about 30%, about 40%, about 50%, about 60% or about 75% relative the efficiency of the lysis of bacterial cells by the lysis reagent in the absence of the agent. In other embodiments, an agent that enhances the lysis of a bacterial cell by a lysis reagent the increases the efficiency of the lysis of bacterial cells by the lysis reagent by about 10% to about 50%, about 10% to about 75%, about 25% to about 75%, about 25% to about 50%, about 25% to about 40%, about 25% to about 30% or about 50% or about 75% relative the efficiency of the lysis of bacterial cells by the lysis reagent in the absence of the agent. The efficiency of the lysis of bacterial cells by a lysis reagent can be determined by, e.g., measuring the percentage or number of bacterial cells lysed by a lysis reagent using techniques known to one skilled in the art.

In one embodiment, in a composition described herein, an agent that enhances the lysis of a bacterial cell by a lysis reagent is about 1% to about 20% by weight of the total weight of the composition, about 5% to about 20% by weight of the total weight of the composition, about 10% to about 20% by weight of the total weight of the composition, or about 15% to about 20% by weight of the total weight of the composition. In another embodiment, in a composition described herein, an agent that enhances the lysis of a bacterial cell by a lysis reagent is about 1%, about 5%, about 8%, about 10%, about 15%, or about 20% by weight of the total weight of the composition.

In another embodiment, an agent that enhances the lysis of a bacterial cell by a lysis reagent is present in a composition described herein at a concentration of about 0.01 mM to about 10 mM, about 0.05 mM to about 10 mM, about 0.1 mM to about 10 mM, about 0.5 mM to about 10 mM, about 1 mM to about 10 mM, about 2 mM to about 10 mM, about 5 mM to about 10 mM, or about 8 to about 10 mM after rehydration. In another embodiment, an agent that enhances the lysis of a bacterial cell by a lysis reagent is present in a composition described herein at a concentration of about 0.01 mM to about 5 mM, about 0.05 mM to about 5 mM, about 0.1 mM to about 5 mM, about 1 mM to about 4 mM, about 1 mM to about 3 mM, about 2 mM to about 3 mM, about 0.1 mM to about 2 mM, or about 0.01 mM to about 1 mM after rehydration. In another embodiment, an agent that enhances the lysis of a bacterial cell by a lysis reagent is present in a composition described herein at a concentration of about 0.01 mM, about 0.05 mM, about 0.1 mM, about 0.5 mM, about 1 mM, about 2 mM, about 3 mM, about 4 mM, about 5 mM, about 6 mM, about 7 mM, about 8 mM, about 9 mM, or about 10 mM after rehydration. In another embodiment, a composition comprises an agent that enhances the lysis of a bacterial cell by a lysis reagent is present in a composition described herein at a concentration of about 0.1 mM to about 5 mM, about 1 mM to about 4 mM, about 1 mM to about 3 mM, about 2 mM to about 3 mM, or about 0.1 to about 2 mM.

In a specific embodiment, a composition comprises a lysis reagent (e.g., lysozyme, labiase, lysostaphin, achromopeptidase, or mutanolysin), an agent that promotes the stabilization of the lysis reagent, EDTA or EGTA, and one or more intracellular bacterial target detection reagents. In another specific embodiment, a composition comprises lysozyme, trehalose, EDTA, and one or more intracellular bacterial target detection reagents.

In a specific embodiment, a composition comprises lysozyme, trehalose and one or more intracellular bacterial target detection reagents. In a particular embodiment, a composition described herein comprises: (i) about 5% to about 30% of lysozyme by weight of the total weight of the composition, about 5% to about 25% of lysozyme by weight of the total weight of the composition, about 5% to about 20% of lysozyme by weight of the total weight of the composition, about 5% to about 15% of lysozyme by weight of the total weight of the composition, or about 5% to about 10% of lysozyme by weight of the total weight of the composition; (ii) about 20% to about 70% of trehalose by weight of the total weight of the composition, about 20% to about 65% of trehalose by weight of the total weight of the composition, about 20% to about 60% of trehalose by weight of the total weight of the composition, about 20% to about 50% of trehalose by weight of the total weight of the composition, about 20% to about 40% of trehalose by weight of the total weight of the composition, about 20% to about 30% of trehalose by weight of the total weight of the composition, or about 20% to about 25% of trehalose by weight of the total weight of the composition; (iii) about 1% to about 20% of EDTA by weight of the total weight of the composition, about 5% to about 20% of EDTA by weight of the total weight of the composition, about 10% to about 20% of EDTA by weight of the total weight of the composition, or about 15% to about 20% of EDTA by weight of the total weight of the composition; and (iv) one or more intracellular bacterial target detection reagents. In another embodiment, a composition described herein comprises: (i) a concentration of about 10 mg/ml to about 100 mg/ml, about 10 mg/ml to about 75 mg/ml, about 10 mg/ml to about 60 mg/ml, about 10 mg/ml to about 50 mg/ml, about 10 mg/ml to about 40 mg/ml, about 10 mg/ml to about 30 mg/ml, about 10 mg/ml to about 25 mg/ml or about 10 mg/ml to about 15 mg/ml of lysozyme after rehydration; (ii) a concentration of about 10 mg/ml to about 100 mg/ml, about 25 mg/ml to about 100 mg/ml, about 50 mg/ml to about 100 mg/ml, about 75 mg/ml to about 100 mg/ml or about 85 mg/ml to about 100 mg/ml of trehalose after rehydration; (iii) about 0.01 mM to about 10 mM, about 0.05 mM to about 10 mM, about 0.1 mM to about 10 mM about 0.5 mM to about 10 mM, about 1 mM to about 10 mM, about 2 mM to about 10 mM, about 5 mM to about 10 mM, or about 8 to about 10 mM of EDTA after rehydration; and (iv) one or more intracellular bacterial target detection reagents.

In another embodiment, a composition described herein comprises: (i) a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme after rehydration; (ii) about 0.1% to about 10%, about 1% to about 10%, about 2% to about 10%, about 4% to about 10%, about 1% to about 8%, about 2% to about 8%, about 2% to about 6%, or about 2% to about 4% of trehalose by weight of the total weight of the composition; (iii) a concentration of about 0.1 mM to about 5 mM, about 1 mM to about 4 mM, about 1 mM to about 3 mM, about 2 mM to about 3 mM, or about 0.1 to about 2 mM of EDTA after rehydration; and (iv) one or more intracellular bacterial target detection reagents. In another embodiment, a composition described herein comprises: (i) a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme after rehydration; (ii) a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose by weight of the total weight of the composition; (iii) a concentration of about 0.1 mM to about 5 mM, about 1 mM to about 4 mM, about 1 mM to about 3 mM, about 2 mM to about 3 mM, or about 0.1 to about 2 mM of EDTA after rehydration; (iv) and one or more intracellular bacterial target detection reagents.

In another embodiment, a composition described herein comprises a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme after rehydration, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose after rehydration, a concentration of about 0.1 mM to about 5 mM, about 1 mM to about 4 mM, about 1 mM to about 3 mM, about 2 mM to about 3 mM, or about 0.1 to about 2 mM of EDTA after rehydration, and one or more intracellular bacterial target detection reagents. In another embodiment, a composition described herein comprises a concentration of about 0.1 mg/ml to about 8 mg/ml, about 1 mg/ml to about 6 mg/ml, about 1 mg/ml to about 5 mg/ml, about 1 mg/ml to about 5 mg/ml, about 2 mg/ml to 4 mg/ml, or about 3 mg/ml of lysozyme after rehydration, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose after rehydration, a concentration of about 0.1 mM to about 5 mM, about 1 mM to about 4 mM, about 1 mM to about 3 mM, about 2 mM to about 3 mM, or about 0.1 to about 2 mM of EDTA after rehydration, and one or more intracellular bacterial target detection reagents.

In another embodiment, a composition described herein comprises a concentration of about 0.1 mg/ml to about 10 mg/ml, about 0.5 mg/ml to about 10 mg/ml, about 1 mg/ml to about 10 mg/ml, about 2 mg/ml to about 10 mg/ml, about 3 mg/ml to about 10 mg/ml, about 4 mg/ml to about 10 mg/ml or about 5 mg/ml to about 10 mg/ml of lysozyme, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose, a concentration of about 0.1 mM to about 5 mM, about 1 mM to about 4 mM, about 1 mM to about 3 mM, about 2 mM to about 3 mM, or about 0.1 to about 2 mM of EDTA, and one or more intracellular bacterial target detection reagents. In another embodiment, a composition described herein comprises a concentration of about 0.1 mg/ml to about 8 mg/ml, about 1 mg/ml to about 6 mg/ml, about 1 mg/ml to about 5 mg/ml, about 1 mg/ml to about 4 mg/ml, about 2 mg/ml to 4 mg/ml, or about 3 mg/ml of lysozyme, a concentration of about 0.1% to about 10%, about 1% to about 10%, about 2% to about 10%, about 4% to about 10%, about 1% to about 8%, about 2% to about 8%, about 2% to about 6%, or about 2% to about 4% of trehalose, a concentration of about 0.1 mM to about 5 mM, about 1 mM to about 4 mM, about 1 mM to about 3 mM, about 2 mM to about 3 mM, or about 0.1 to about 2 mM of EDTA, and one or more intracellular bacterial target detection reagents.

In some embodiments, the compositions described herein may include a buffer. Any buffer that aids in maintaining the pH of the composition and does not interfere with the ability of an intracellular bacterial target to be detected may be used. Non-limiting examples of butlers include phosphate MES buffer, acetate buffer, Tris buffer, ADA buffer, MDPS buffer, and HEPES butler. In one embodiment, a composition comprises 0.05 to 1 ml of phosphate or MES buffer. In a specific embodiment, a composition described herein is about pH 5 to about pH 8, preferably about pH 5.5 to about pH 7.5, and more preferably pH 6 to about pH 7.

In another embodiment, a composition comprises about 10 mM to about 200 mM, about 25 mM to about 200 mM, about 50 mM to about 200 mM, about 75 mM to about 200 mM, about 100 mM to about 200 mM, about 125 mM to about 200 mM, about 150 mM to 200 mM, or about 175 mM to about 200 mM of buffer (e.g., phosphate or MES buffer) after rehydration. In another embodiment, a composition comprises about 10 mM, about 25 mM, about 50 mM, about 75 mM, about 100 mM, about 125 mM, about 150 mM, about 175 mM, or about 200 mM of buffer (e.g., phosphate or MES buffer) after rehydration.

In some embodiments, a composition described herein may comprise an agent that assists with the identification of a particular class, type or subtype of a particular intracellular bacterial target. For example, if the intracellular bacterial target is a beta-lactamase, a composition may comprise one or more inhibitors of certain types of beta-lactamases in addition to a beta-lactamase substrate and a lysis reagent.

Although the compositions described herein are with respect to intracellular bacterial targets, the compositions may include, in addition to or in place of an intracellular bacterial target detection reagent, reagents necessary for the detection of a bacterial target (e.g., protein, peptide, lipid, carbohydrate, or fatty acid) that is expressed, present or located on the surface of a bacteria. One skilled in the art would know what reagents could be used to detect bacterial targets expressed, present or located on the cell surface.

In some embodiments, a composition described herein is filtered using, e.g., a 0.2 micron filter. A composition described herein may or may not be filtered prior to drying the composition. In certain embodiments, a composition described herein is subjected to gamma irradiation, or is autoclaved. In other embodiments, a composition described herein is not subjected to any process that adversely affects the activity of one or more of the components of the composition (e.g., an enzyme that promotes the lysis of a bacterial cell). A composition described herein may or may not subjected to gamma irradiation or autoclaved before drying the composition. In specific embodiments, a composition described herein is not subjected to gamma irradiation, or is not autoclaved.

In some embodiments, a composition described herein is dried on or in a solid support using heat at temperatures of, e.g., about 50° C. to about 100° C., about 50° C. to about 85° C., about 50° C. to about 75° C., about 60° C. to about 75° C., or about 60° C. to about 70° C. In one embodiment, a composition described herein is dried on or in a solid support using heat under forced air or vacuum conditions at temperatures of, e.g., about 50° C. to about 100° C., about 50° C. to about 85° C., about 50° C. to about 75° C., about 60° C. to about 75° C., or about 60° C. to about 70° C. In other embodiments, a composition described herein is dried on or in a solid support using a lypholization technique. In other embodiments, a composition described herein is dried on or in a solid support using a spray drying technique.

In one embodiment, a composition described herein is dried and is present in or on a paper disk or paper strip. In certain embodiments, a paper disk or paper strip is divided up into different sections with each section having a different dried composition. For example, the paper disk or paper strip may comprise three sections with each section comprising a different dried composition comprising an intracellular bacterial target detection reagent and a lysis reagent. In another embodiment, there is only one composition per paper disk or paper strip. In other words, each paper disk or paper strip only comprises one dried composition. In a specific embodiment, the paper disk or paper strip is filter paper. In another specific embodiment, a composition presented herein dried and is present in a BBL™ Dryslide™ Nitrocefin (Becton Dickinson, Diagnostic Systems, USA), or a solid support similar to a BBL™ Dryslide™ Nitrocefin (Becton Dickinson, Diagnostic Systems, USA).

In certain embodiments, a composition described herein is dried and present in a well of a panel, a tray, a cassette or a plate (e.g., a microtiter plate). In some embodiments, different wells of a panel, a tray, a cassette or a plate contain a different dried composition. In specific embodiments, a composition described herein is dried and is present in a well of a tray, a panel, a tray or a cassette, such as a well of a Phoenix™ Panel (BD, USA), a well of a panel of a BBL™ Crystal™ Identification System (BD, USA), a Vitek® card (bioMerieux, USA), a well of a MicroScan panel (Dade Behring, USA), or a well of a panel of a Remel RapID™ System (Remel, USA). See, e.g., U.S. Pat. Nos. 5,922,593 and Des. 421,498 (each of which are incorporated herein by reference) for an exemplary description of panels with wells that a composition described herein may be dried into using, e.g., heat.

In a particular embodiment, a composition described herein is dried and is present in a well of a Phoenix™ Panel (BD, USA) and an automated system, such as the BD Phoenix™ Automated Microbiology System (BD, USA), is used to detect the presence of an intracellular bacterial target. See, e.g., U.S. Pat. Nos. 5,922,593, 6,096,272, 6,372,485 and 7,115,384 (each of which are incorporated herein by reference) for a description of an automated system for detection of an intracellular bacterial target.

In some embodiments, a composition described herein is dried and is present in a well of a panel of BBL™ Crystal™ Identification System (BD, USA) and an automated system, such as BBL™ Crystal™ Identification System (BD, USA), is used to detect the presence of an intracellular bacterial target. In other embodiments, a composition described herein is dried and is present in a well of a Vitek® card (bioMerieux, USA) and an automated system, such as the Vitek® card (bioMerieux, USA), is used to detect the presence of an intracellular bacterial target. In other embodiments, a composition described herein is dried and is present in a well of a MicroScan panel (Dade Behring, USA) and an automated system, such as the MicroScan Walk-Away® system, is used to detect the presence of an intracellular bacterial target.

In certain embodiments, a composition described herein is dried and is present in a tube, e.g., a test tube or eppendorf. In a specific embodiment, a composition described herein is dried and is present in a tube of an API biochemical test (bioMerieux, USA).

In certain embodiments, a composition described herein is in the form of a dry powder. The dry powder and a bacterial cell suspension may be combined in any type of container (e.g., the wells of a microtiter plate, a test tube, or an Eppendorf tube), and an intracellular bacterial target may be detected by an appropriate technique or device which will vary depending upon the intracellular bacterial target detection reagent chosen.

In certain embodiments, a composition described herein is used to form a tablet. The tablet and a bacterial cell suspension may be combined in any type of container (e.g., the wells of a microtiter plate, a test tube, or an Eppendorf tube), and an intracellular bacterial target may be detected by an appropriate technique or device which will vary depending upon the intracellular bacterial target detection reagent chosen.

4.2.2.1 Intracellular Bacterial Target Detection Reagents

Intracellular bacterial target detection reagents for use in the detection of intracellular bacterial targets are known to those skilled in the art. In some embodiments, the intracellular bacterial target detection reagent is membrane impermeable. In other embodiments, the intracellular bacterial target detection reagent is membrane permeable. In some embodiments, the presence of a lysis reagent increases the rate of utilization of an intracellular bacterial target detection reagent by an intracellular bacterial target. In one embodiment, the intracellular bacterial target detection reagent is a substrate for an intracellular bacterial target. For example, the intracellular bacterial target detection reagent is a substrate that the intracellular bacterial target hydrolyzes. In another embodiment, the intracellular bacterial target detection reagent forms a complex with an intracellular bacterial target which is detectable.

In one embodiment, one of the intracellular bacterial target detection reagents included in a composition described herein is a beta-lactamase substrate. Any substrate for beta-lactamase that is readily detectable may be used in the compositions presented herein. One skilled in the art will know how to use a given beta-lactamase substrate in the detection of a beta-lactamase. In particular, one of skill in the art will appreciate that the method for detecting the utilization of a beta-lactamase substrate will depend upon the beta-lactamase substrate chosen.

Non-limiting examples of detectable beta-lactamase substrates include chromogenic substrates, fluorogenic substrates, and antibiotics. Chromogenic beta-lactamase substrates include, but are not limited to, nitrocefin (3-[2,4-dinitrostyryl]-7-(2-thienylacetamido]3-cephem-4-carboxylic acid (Calbiochem, San Diego, Calif.)), PADAC® (Pyridinium-2-azo-p-dimethylaniline chromophore (Calbiochem, San Diego, Calif.)), CENTA™ (EMD Chemicals, Inc., San Diego, Calif.), HMRZ-86 (((7R)-7[2-aminothiazol-4-yl]-(z)-2-(1-carboxy-1-methylethoxyimino)acetamido)-3-(2,4-dinitrostyryl)-3-cephem-4-carboxylic acid trifluoroacetate, E-isomer (Kanto Chemical Co., Inc. Tokyo, Japan)), and cefesone. Fluorogenic substrates include, but are not limited to, Fluorcillin Green 495/525 and Fluorocillin Green 345/350 LIVE BLAZER™-FRET B/G (Invitrogen, Carlsbad, Calif.). Antibiotics include beta-lactams, penicillin, amoxicillin, etc.

In a specific embodiment, the detectable beta-lactamase substrate is nitrocefin. In an embodiment, a composition described herein comprises about 0.01% to about 1%, about 0.05% to about 1%, or about 0.75% to about 1% of nitrocefin by weight of the total weight of the composition. In another embodiment, a composition described herein comprises about 0.01%, about 0.02%, about 0.05%, about 0.75%, about 0.90% or about 1% of nitrocefin by weight of the total weight of the composition. In another embodiment, nitrocefin is present in a composition described herein at a concentration of about 20 μM to about 200 μM after rehydration. In another embodiment, nitrocefin is present in a composition described herein at a concentration of about 1 μM to about 1 mM, about 1 μM to about 750 μM, about 1 μM to about 500 μM, or about 1 μM to about 250 μM. In another embodiment, nitrocefin is present in a composition described herein at a concentration of about 1 μM to about 1 mM, about 1 μM to about 750 μM, about 1 μM to about 500 μM, or about 1 μM to about 250 μM after rehydration. In another embodiment, nitrocefin is present in a composition described herein at a concentration of about 20 μM to about 200 μM. In another embodiment, nitrocefin is present in a composition described herein at a concentration of about 20 μM to about 200 μM after rehydration. In another embodiment, nitrocefin is present in a composition described herein at a concentration of about 0.05 mM after rehydration.

In another embodiment, the detectable beta-lactamase substrate is CENTA™. In an embodiment, a composition described herein comprises about 0.01% to about 1%, about 0.05% to about 1%, or about 0.75% to about 1% of CENTA™ by weight of the total weight of the composition. In another embodiment, a composition described herein comprises about 0.01%, about 0.02%, about 0.05%, about 0.75%, about 0.90% or about 1% of CENTA™ by weight of the total weight of the composition. In another embodiment, CENTA™ is present in a composition described herein at a concentration of about 1 μM to about 1 mM, about 1 μM to about 750 μM, about 1 μM to about 500 μM, or about 1 μM to about 250 μM. In another embodiment, CENTA™ is present in a composition described herein at a concentration of about 1 μM to about 1 mM, about 1 μM to about 750 μM, about 1 μM to about 500 μM, or about 1 to about 250 μM after rehydration. In another embodiment, CENTA™ is present in a composition described herein at a concentration of about 20 μM to about 200 μM. In another embodiment, CENTA™ is present in a composition described herein at a concentration of about 20 μM to about 200 μM after rehydration. In another embodiment, CENTA™ is present in a composition described herein at a concentration of about 0.05 mM after rehydration.

In another embodiment, the detectable beta-lactamase substrate is HMRZ-86. In an embodiment, a composition described herein comprises about 0.01% to about 1%, about 0.05% to about 1%, or about 0.75% to about 1% of HMRZ-86 by weight of the total weight of the composition. In another embodiment, a composition described herein comprises about 0.01%, about 0.02%, about 0.05%, about 0.75%, about 0.90% or about 1% of HMRZ-86 by weight of the total weight of the composition. In another embodiment, HMRZ-86 is present in a composition described herein at a concentration of about 1 μM to about 1 mM, about 1 μM to about 750 μM, about 1 μM to about 500 μM, or about 1 μM to about 250 μM. In another embodiment, HMRZ-86 is present in a composition described herein at a concentration of about 1 μM to about 1 mM, about 1 μM to about 750 μM, about 1 μM to about 500 μM, or about 1 μM to about 250 μM after rehydration. In another embodiment, HMRZ-86 is present in a composition described herein at a concentration of about 20 μM to about 200 μM. In another embodiment, HMRZ-86 is present in a composition described herein at a concentration of about 20 μM to about 200 μM after rehydration. In another embodiment, HMRZ-86 is present in a composition described herein at a concentration of about 0.05 mM after rehydration.

In certain embodiments, one of the intracellular bacterial target detection reagents included in a composition described herein is not a beta-lactamase substrate.

In another embodiment, one of the intracellular bacterial target detection reagents included in a composition described herein is a peptidase substrate. Any substrate for a peptidase that is readily detectable may be used in the compositions presented herein. One skilled in the art will know how to use a given peptidase substrate in the detection of a peptidase. In particular, one of skill in the art will appreciate that the method for detecting the utilization of a peptidase substrate will depend upon the peptidase substrate chosen.

Non-limiting examples of detectable peptidase substrates include L-seryl-L-tyrosine 7 amido-4-methylcoumarin, N-4-tosyl-glycyl-L-prolyl-L-arginine 7-amido-4-methylcoumarin hydrochloride and L-arginyl-L-arginine 7-amido-4-methylcoumarin trihydrochloride. In some embodiments, a peptidase substrate is present in a composition presented herein at a concentration of about 0.1 μM to about 1 mM, about 0.1 μM to about 750 μM, about 0.1 μM to about 500 μM, about 0.1 μM to about 250 μM, about 0.1 μM to about 100 μM, or about 0.1 μM to about 10 μM. In certain embodiments, a peptidase substrate is present in a composition presented herein at a concentration of about 0.1 μM to about 1 mM, about 0.1 μM to about 750 μM, about 0.1 μM to about 500 μM, about 0.1 μM to about 250 μM, about 0.1 μM to about 100 μM, or about 0.1 μM to about 10 μM after rehydration. In some embodiments, a peptidase substrate is present in a composition described herein at a concentration of about 0.05 mM after rehydration. In certain embodiment, a composition described herein comprises about 0.01% to about 1%, about 0.05% to about 1%, or about 0.75% to about 1% of a peptidase substrate by weight of the total weight of the composition. In other embodiments, a composition described herein comprises about 0.01%, about 0.02%, about 0.05%, about 0.75%, about 0.90% or about 1% of a peptidase substrate by weight of the total weight of the composition.

In another embodiment, one of the intracellular bacterial target detection reagents included in a composition described herein is an esterase substrate. Any substrate for esterase that is readily detectable may be used in the compositions presented herein. One skilled in the art will know how to use a given esterase substrate in the detection of an esterase. In particular, one of skill in the art will appreciate that the method for detecting the utilization of an esterase substrate will depend upon the esterase substrate chosen.

Non-limiting examples of detectable esterase substrates include chromogenic substrates and fluorogenic substrates. Chromogenic substrates include, but are not limited to, 6-chloro-3-indoxyl palmitate, 5-bromo-6-chloro-3-indoxy palmitate, and 6-chloro-3-indoxyl nonanoate. Fluorogenic substrates include, but are not limited to, 4-methylumbelliferyl palmitate and 4-methylumbelliferyl nonanoate. In some embodiments, an esterase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM. In certain embodiments, an esterase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM after rehydration. In some embodiments, an esterase substrate is present in a composition described herein at a concentration of about 0.05 mM after rehydration. In certain embodiment, a composition described herein comprises about 0.01% to about 1%, about 0.05% to about 1%, or about 0.75% to about 1% of an esterase substrate by weight of the total weight of the composition. In other embodiments, a composition described herein comprises about 0.01%, about 0.02%, about 0.05%, about 0.75%, about 0.90% or about 1% of an esterase substrate by weight of the total weight of the composition.

In another embodiment, one of the intracellular bacterial target detection reagents included in a composition described herein is a glucose oxidase substrate. Any substrate for glucose oxidase that is readily detectable may be used in the compositions presented herein. One skilled in the art will know how to use a given glucose oxidase substrate in the detection of glucose oxidase substrate. In particular, one of skill in the art will appreciate that the method for detecting the utilization of a glucose oxidase substrate will depend upon the glucose oxidase substrate chosen.

A non-limiting example of a glucose oxidase substrate is nitrotetrazolium blue chloride. In some embodiments, a glucose oxidase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM. In certain embodiments, a glucose oxidase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM after rehydration. In some embodiments, a glucose oxidase substrate is present in a composition described herein at a concentration of about 0.05 mM after rehydration. In certain embodiment, a composition described herein comprises about 0.01% to about 1%, about 0.05% to about 1%, or about 0.75% to about 1% of a glucose oxidase substrate by weight of the total weight of the composition. In other embodiments, a composition described herein comprises about 0.01%, about 0.02%, about 0.05%, about 0.75%, about 0.90% or about 1% of a glucose oxidase substrate by weight of the total weight of the composition.

In another embodiment, one of the intracellular bacterial target detection reagents included in a composition described herein is a beta-glucosidase substrate. Any substrate for beta-glucosidase that is readily detectable may be used in the compositions presented herein. One skilled in the art will know how to use a given beta-glucosidase substrate in the detection of beta-glucosidase. In particular, one of skill in the art will appreciate that the method for detecting the utilization of a beta-glucosidase substrate will depend upon the beta-glucosidase substrate chosen.

Non-limiting examples of beta-glucosidase substrate include 2-nitrophenyl beta-D-glucopyranoside, 3-acetylumbelliferyl beta-D-glucopyranoside, 4-methylumbelliferyl beta-D-glucopyranoside, and 5-bromo-4-chloro-3-indolyl beta-D-glucopyranoside. In some embodiments, a beta-glucosidase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM. In certain embodiments, a beta-glucosidase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM after rehydration. In some embodiments, a beta-glucosidase substrate is present in a composition described herein at a concentration of about 0.05 mM after rehydration. In certain embodiment, a composition described herein comprises about 0.01% to about 1%, about 0.05% to about 1%, or about 0.75% to about 1% of a beta-glucosidase substrate by weight of the total weight of the composition. In other embodiments, a composition described herein comprises about 0.01%, about 0.02%, about 0.05%, about 0.75%, about 0.90% or about 1% of a beta-glucosidase substrate by weight of the total weight of the composition.

In another embodiment, one of the intracellular bacterial target detection reagents included in a composition described herein is a glucuronidase substrate. Any substrate for glucuronidase that is readily detectable may be used in the compositions presented herein. One skilled in the art will know how to use a given glucuronidase substrate in the detection of a glucuronidase. In particular, one of skill in the art will appreciate that the method for detecting the utilization of a glucoronidase substrate will depend upon the glucuronidase substrate chosen.

A non-limiting example of a glucuronidase substrate is 4-nitrophenyl beta-D-fucopyranoside. In some embodiments, a glucoronidase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM. In certain embodiments, a glucoronidase substrate is present in a composition presented herein at a concentration of about 0.1 µM to about 1 mM, about 0.1 µM to about 750 µM, about 0.1 µM to about 500 µM, about 0.1 µM to about 250 µM, about 0.1 µM to about 100 µM, or about 0.1 µM to about 10 µM after rehydration. In some embodiments, a glucoronidase substrate is present in a composition described herein at a concentration of about 0.05 mM after rehydration. In certain embodiment, a composition described herein comprises about 0.01% to about 1%, about 0.05% to about 1%, or about 0.75% to about 1% of a glucoronidase substrate by weight of the total weight of the composition. In other embodiments, a composition described herein comprises about 0.01%, about 0.02%, about 0.05%, about 0.75%, about 0.90% or about 1% of a glucoronidase substrate by weight of the total weight of the composition.

In some embodiments, a composition described herein comprises two or more intracellular bacterial target detection reagents and such a composition is present in a dry form in or on a solid support, such as a well of a plate, a tray, a panel or a cassette, a tube, a paper disk or a paper strip. In some embodiments, a composition described herein comprises two or more intracellular bacterial target detection reagents and such a composition is in the form of a tablet or a dry powder. In a specific embodiment, the presence of the two or more intracellular bacterial target detection reagents enables one to detect the presence of two or more intracellular bacterial targets.

4.3 Detection of Intracellular Microorganism Targets

In one aspect, presented herein are methods for the detection of an intracellular microorganism target utilizing a solid support described herein containing a dry composition which provides reagents for lysing a microbe as well as reagents for the detection of an intracellular microorganism target. In accordance with this aspect, the dry composition may be present in or on the solid support. In a specific embodiment, a method for detecting the presence of an intracellular microorganism target, comprises (a) contacting a microorganism sample with a composition described herein that is dried and is present on or in a solid support; and (b) detecting the utilization of an intracellular microorganism target detection reagent, wherein the utilization of the intracellular microorganism target detection reagent indicates the presence of the intracellular microorganism target. In certain embodiments, the dried composition is rehydrated prior to or concurrently with the step of contacting the microorganism sample with the composition. The dried composition may be rehydrated using, e.g., a buffer, a saline buffer, a media, or sterile water. In other embodiments, the microorganism sample used is a microbial suspension and the suspension is contacted with the dried composition.

In a specific aspect, presented herein are methods for the detection of an intracellular bacterial target utilizing a solid support described herein containing a dried composition which provides reagents necessary to lyse a bacterial cell as well as reagents necessary to detect an intracellular bacterial target. In a specific embodiment, a method for detecting the presence of an intracellular bacterial target, comprises (a) contacting a bacterial sample with a composition described herein that is dried and is present on or in a solid support; and (b) detecting the utilization of an intracellular bacterial target detection reagent, wherein the utilization of the intracellular bacterial target detection reagent indicates the presence of the intracellular bacterial target. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition.

In a specific embodiment, a method for detecting the presence of an intracellular bacterial target, comprises (a) contacting a bacterial sample with a composition described herein that is dried and is present on or in a paper strip or a paper disk; and (b) detecting the utilization of an intracellular bacterial target detection reagent, wherein the utilization of the intracellular bacterial target detection reagent indicates the presence of the intracellular bacterial target. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In other embodiments, the bacterial sample is an inoculum of bacteria and it is smeared on the paper disk or paper strip in the absence of any hydration.

In a specific embodiment, a method for detecting the presence of an intracellular bacterial target, comprises (a) contacting a bacterial sample with a composition described herein that is dried and is present on or in a well; and (b) detecting the utilization of an intracellular bacterial target detection reagent, wherein the utilization of the intracellular bacterial target detection reagent indicates the presence of the intracellular bacterial target. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition.

In another aspect, presented herein are methods for the detection of an intracellular microorganism target utilizing a tablet comprising reagents necessary to lyse a microbe as well as reagents necessary to detect an intracellular microorganism target. In another embodiment, a method for detecting the presence of an intracellular microorganism target, comprises (a) contacting a tablet comprising a composition described herein; and (b) detecting the utilization of an intracellular microorganism target detection reagent, wherein the utilization of the intracellular microorganism target detection reagent indicates the presence of the intracellular microorganism target. In certain embodiments, the tablet is hydrated prior to or concurrently with the step of contacting the microorganism sample with the tablet. The tablet may be hydrated using, e.g., a buffer, a saline buffer, a media, or sterile water. In other embodiments, the microorganism sample used is a microbial suspension and the suspension is contacted with the tablet.

In a specific aspect, presented herein are methods for the detection of an intracellular bacterial target utilizing a tablet comprising reagents necessary to lyse a bacterial cell as well as reagents necessary to detect an intracellular bacterial target. In another embodiment, a method for detecting the presence of an intracellular bacterial target, comprises (a) contacting a tablet comprising a composition described herein; and (b) detecting the utilization of an intracellular bacterial target detection reagent, wherein the utilization of the intracellular bacterial target detection reagent indicates the presence of the intracellular bacterial target. In certain embodiments, the tablet is hydrated prior to or concurrently with the step of contacting the bacterial sample with the tablet. The tablet may be hydrated using, e.g., a buffer, a saline buffer, a media, or sterile water. In other embodiments, the bacterial sample used is a bacterial cell suspension and the suspension is contacted with the dried composition.

In another aspect, presented herein are methods for the detection of an intracellular microorganism target utilizing a dry powder comprising reagents necessary to lyse a microbe as well as reagents necessary to detect an intracellular bacterial target. In a specific embodiment, a method for detecting the presence of an intracellular microorganism target, comprises (a) contacting a microorganism sample with a composition described herein that is in the form of a dry powder; and (b) detecting the utilization of an intracellular microorganism target detection reagent, wherein the utilization of the intracellular microorganism target detection reagent indicates the presence of the intracellular microorganism target. In certain embodiments, the dry powder is hydrated prior to or concurrently with the step of contacting the microorganism sample with the dry powder. The dried powder may be hydrated using, e.g., a buffer, a saline buffer, a media, or sterile water. In other embodiments, the microorganism sample used is a microbial suspension and the suspension is contacted with the dry powder.

In a specific aspect, presented herein are methods for the detection of an intracellular bacterial target utilizing a dry powder comprising reagents necessary to lyse a bacterial cell as well as reagents necessary to detect an intracellular bacterial target. In a specific embodiment, a method for detecting the presence of an intracellular bacterial target, comprises (a) contacting a bacterial sample with a composition described herein that is in the form of a dry powder; and (b) detecting the utilization of an intracellular bacterial target detection reagent, wherein the utilization of the intracellular bacterial target detection reagent indicates the presence of the intracellular bacterial target. In certain embodiments, the dried composition is rehydrated prior to or concurrently with the step of contacting the bacterial sample with the composition. The dry powder may be hydrated using, e.g., a buffer, a saline buffer, a media, or sterile water. In other embodiments, the bacterial sample used is a bacterial cell suspension and the suspension is contacted with the dry powder The methods for the detection of an intracellular microorganism target can also be used to detect microorganism targets (e.g., proteins, peptides, lipids, carbohydrates, or fatty acids) expressed, present, or located on the surface of a microorganism. In particular, the methods for the detection of an intracellular bacterial target can also be used to detect bacterial targets (e.g., proteins, peptides, lipids, carbohydrates, or fatty acids) expressed, present or located on the surface of a bacteria. For example, compositions comprising a lysis reagent and a reagent to detect the presence of a bacterial target, which are dried and are present on or in a solid support, or in the form of a tablet or dry powder, may be used to detect the presence of a bacterial target, regardless of whether the bacterial target is intracellular. Such compositions may further comprise an agent that promotes the stabilization of the lysis reagent.

In one embodiment, presented herein are methods for detecting the presence of a beta-lactamase in a bacterial source utilizing a solid substrate comprising a dried composition described herein. In a specific embodiment, a method for detecting the presence of a beta-lactamase in a bacterial source comprises: (a) contacting a bacterial sample with a composition that is dried and is present in or on a solid support, wherein the composition comprises a lysis reagent and a beta-lactamase substrate; and (b) detecting utilization of the substrate in the composition, wherein substrate utilization in the composition indicates the presence of a beta-lactamase in the bacterial source. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In another embodiment, presented herein are methods for detecting the presence of a beta-lactamase in a bacterial source utilizing a tablet comprising a composition described herein. In a specific embodiment, a method for detecting the presence of a beta-lactamase in a bacterial source comprises (a) contacting a bacterial sample with a tablet comprising a composition, wherein the composition comprises a lysis reagent and a beta-lactamase substrate; and (b) detecting utilization of the substrate in the composition, wherein substrate utilization in the composition indicates the presence of a beta-lactamase in the bacterial source. In certain embodiments, the tablet is hydrated prior to or concurrently with the step of contacting the bacterial sample with the tablet. The tablet may be hydrated using, e.g., a buffer, a saline buffer, a media, or sterile water. In other embodiments, the bacterial sample used is a bacterial cell suspension and the suspension is contacted with the tablet. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of a beta-lactamase in a bacterial source utilizing a composition described herein in the form of a dry powder. In a specific embodiment, a method for detecting the presence of a beta-lactamase in a bacterial source comprises (a) contacting a bacterial sample with a composition in the form of a dry powder, wherein the composition comprises a lysis reagent and a beta-lactamase substrate; and (b) detecting utilization of the substrate in the composition, wherein substrate utilization in the composition indicates the presence of a beta-lactamase in the bacterial source. In certain embodiments, the dry powder is hydrated prior to or concurrently with the step of contacting the bacterial sample with the dry powder. The dry powder may be hydrated using, e.g., a buffer, a saline buffer, a media, or sterile water. In other embodiments, the bacterial sample used is a bacterial cell suspension and the suspension is contacted with the dry powder. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of a peptidase in a bacterial source utilizing a solid substrate comprising a dried composition described herein. In a specific embodiment, a method for detecting the presence of a peptidase in a bacterial source comprises: (a) contacting a bacterial sample with a composition that is dried and is present on or in a solid support, wherein the composition comprises a lysis reagent and a peptidase substrate; and (b) detecting utilization of the substrate in the composition, wherein substrate utilization in the composition indicates the presence of a peptidase in the bacterial source. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of a peptidase in a bacterial source utilizing a tablet comprising a composition described herein. In a specific embodiment, a method for detecting the presence of a peptidase in a bacterial source comprises: (a) contacting a bacterial sample with a tablet comprising a composition, wherein the composition comprises a lysis reagent and a peptidase substrate; and (b) detecting utilization of the substrate in the composition, wherein substrate utilization in the composition indicates the presence of a peptidase in the bacterial source. In certain embodiments, the tablet is hydrated prior to or concurrently with the step of contacting the bacterial sample with the tablet. The tablet may be hydrated using, e.g., a buffer, a saline buffer, a media, or sterile water. In other embodiments, the bacterial sample used is a bacterial cell suspension and the suspension is contacted with the tablet. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of a peptidase in a bacterial source utilizing a composition described herein in the form of a dry powder. In a specific embodiment, a method for detecting the presence of a peptidase in a bacterial source comprises: (a) contacting a bacterial sample with a composition in the form of a dry powder, wherein the composition comprises a lysis reagent and a peptidase substrate; and (b) detecting utilization of the substrate in the composition, wherein substrate utilization in the composition indicates the presence of a peptidase in the bacterial source. In certain embodiments, the dry powder is hydrated prior to or concurrently with the step of contacting the bacterial sample with the composition. The dry powder may be hydrated using, e.g., a buffer, a saline butler, a media, or sterile water. In other embodiments, the bacterial sample used is a bacterial cell suspension and the suspension is contacted with the dry powder. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of an esterase in a bacterial source utilizing a solid substrate comprising a dried composition described herein. In a specific embodiment, a method for detecting the presence of an esterase in a bacterial source comprises: (a) contacting a bacterial sample with a composition that is dried and is present in or on a solid support, wherein the composition comprises a lysis reagent and an esterase substrate; and (b) detecting utilization of the substrate in the composition, wherein substrate utilization in the composition indicates the presence of an esterase in the bacterial source. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of an esterase in a bacterial source utilizing a tablet comprising a composition described herein. In a specific embodiment, a method for detecting the presence of an esterase in a bacterial source comprises: (a) contacting a bacterial sample with a tablet comprising a composition, wherein the composition comprises a lysis reagent and an esterase substrate; and (b) detecting utilization of the substrate in the composition, wherein substrate utilization in the composition indicates the presence of an esterase in the bacterial source. In certain embodiments, the tablet is hydrated prior to or concurrently with the step of contacting the bacterial sample with the tablet. The tablet may be rehydrated using, e.g., a buffer, a saline buffer, a media, or sterile water. In other embodiments, the bacterial sample used is a bacterial cell suspension and the suspension is contacted with the tablet. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of an esterase in a bacterial source utilizing a composition described herein in the form of a dry powder. In a specific embodiment, a method for detecting the presence of an esterase in a bacterial source comprises: (a) contacting a bacterial sample with a composition in the form of a dry powder, wherein the composition comprises a lysis reagent and a esterase substrate; and (b) detecting utilization of the substrate in the composition, wherein substrate utilization in the composition indicates the presence of a esterase in the bacterial source. In certain embodiments, the dry powder is hydrated prior to or concurrently with the step of contacting the bacterial sample with the dry powder. The dry powder may be rehydrated using, e.g., a buffer, a saline buffer, a media, or sterile water. In other embodiments, the bacterial sample used is a bacterial cell suspension and the suspension is contacted with the dry powder. In certain embodiments, the composition further comprises an agent that promotes the stabilization of the lysis reagent. In other embodiments, the composition further comprises an agent that promotes the stabilization of the lysis reagent and an agent that enhances the lysis of a bacterial cell by a lysis reagent.

In one embodiment, presented herein are methods for detecting the presence of glucose oxidase in a bacterial source utilizing a solid substrate comprising a dried composition described herein. In a specific embodiment, a method for detecting the presence of glucose oxidase in a bacterial source comprises (a) contacting a bacterial sample with a composition that is dried and is present in or on a solid support, wherein the composition comprises a lysis reagent and a glucose oxidase substrate; and (b) detecting utilization of the substrate in the composition, wherein substrate utilization in the composition indicates the presence of glucose oxidase in the bacterial source. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of glucose oxidase in a bacterial source utilizing a tablet comprising a composition described herein. In a specific embodiment, a method for detecting the presence of glucose oxidase in a bacterial source comprises (a) contacting a bacterial sample with a tablet comprising a composition, wherein the composition comprises a lysis reagent and a glucose oxidase substrate; and (b) detecting utilization of the substrate in the composition, wherein substrate utilization in the composition indicates the presence of glucose oxidase in the bacterial source. In certain embodiments, the tablet is hydrated prior to or concurrently with the step of contacting the bacterial sample with the composition. The tablet may be hydrated using, e.g., a buffer, a saline buffer, a media, or sterile water. In other embodiments, the bacterial sample used is a bacterial cell suspension and the suspension is contacted with the tablet. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of glucose oxidase in a bacterial source utilizing a composition described herein in the form of a dry powder. In a specific embodiment, a method for detecting the presence of glucose oxidase in a bacterial source comprises (a) contacting a bacterial sample with a composition in the form of a dry powder, wherein the composition comprises a lysis reagent and a glucose oxidase substrate; and (b) detecting utilization of the substrate in the composition, wherein substrate utilization in the composition indicates the presence of glucose oxidase in the bacterial source. En certain embodiments, the dry powder is hydrated prior to or concurrently with the step of contacting the bacterial sample with the composition. The dry powder may be hydrated using, e.g., a buffer, a saline buffer, a media, or sterile water. In other embodiments, the bacterial sample used is a bacterial cell suspension and the suspension is contacted with the dry powder. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of beta-glucosidase in a bacterial source utilizing a solid substrate comprising added composition described herein. In a specific embodiment, a method for detecting the presence of beta-glucosidase comprises (a) contacting a bacterial sample with a composition that is dried and is present in or on a solid support, wherein the composition comprises a lysis reagent and a beta-glucosidase substrate; and (b) detecting utilization of the substrate in the composition, wherein substrate utilization in the composition indicates the presence of beta-glucosidase in the bacterial source. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of beta-glucosidase in a bacterial source utilizing a tablet comprising a composition described herein. In a specific embodiment, a method for detecting the presence of beta-glucosidase in a bacterial source comprises (a) contacting a bacterial sample with a tablet comprising a composition, wherein the composition comprises a lysis reagent and a beta-glucosidase substrate; and (b) detecting utilization of the substrate in the composition, wherein substrate utilization in the composition indicates the presence of beta-glucosidase in the bacterial source. In certain embodiments, the tablet is hydrated prior to or concurrently with the step of contacting the bacterial sample with the tablet. The tablet may be hydrated using, e.g., a buffer, a saline buffer, a media, or sterile water. In other embodiments, the bacterial sample used is a bacterial cell suspension and the suspension is contacted with the tablet. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of beta-glucosidase in a bacterial source utilizing a composition described herein in the form of a dry powder. In a specific embodiment, a method for detecting the presence of beta-glucosidase in a bacterial source comprises (a) contacting a bacterial sample with a composition in the form of a dry powder, wherein the composition comprises a lysis reagent and a beta-glucosidase substrate; and (b) detecting utilization of the substrate in the composition, wherein substrate utilization in the composition indicates the presence of beta-glucosidase in the bacterial source. In certain embodiments, the dry powder is hydrated prior to or concurrently with the step of contacting the bacterial sample with the dry powder. The dry powder may be hydrated using, e.g., a buffer, a saline buffer, a media, or sterile water. In other embodiments, the bacterial sample used is a bacterial cell suspension and the suspension is contacted with the dry powder. In certain embodiments, the composition further comprises an agent that promotes the stabilization of the lysis reagent. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of glucuronidase in a bacterial source utilizing a solid substrate comprising a dried composition described herein. In a specific embodiment, a method for detecting the presence of glucuronidase in a bacterial source comprises (a) contacting a bacterial sample with a composition that is dried and is present in or on a solid support, wherein the composition comprises a lysis reagent and a glucuronidase substrate; and (b) detecting utilization of the substrate in the composition, wherein substrate utilization in the composition indicates the presence of glucuronidase in the bacterial source. In certain embodiments, the composition further comprises an agent that promotes the stabilization of the lysis reagent. In certain embodiments, the dried composition is rehydrated prior to or concurrently with the step of contacting the bacterial sample with the composition. The dried composition may be rehydrated using, e.g., a buffer, a saline buffer, a media, or sterile water. In other embodiments, the bacterial sample used is a bacterial cell suspension and the suspension is contacted with the dried composition. In a specific embodiment, the composition further comprises a carbohydrate. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of glucuronidase in a bacterial source utilizing a tablet comprising a composition described herein. In a specific embodiment, a method for detecting the presence of glucuronidase in a bacterial source comprises (a) contacting a bacterial sample with a tablet comprising a composition, wherein the composition comprises a lysis reagent and a glucuronidase substrate; and (b) detecting utilization of the substrate in the composition, wherein substrate utilization in the composition indicates the presence of glucuronidase in the bacterial source. In certain embodiments, the tablet is hydrated prior to or concurrently with the step of contacting the bacterial sample with the tablet. The tablet may be hydrated using, e.g., a buffer, a saline buffer, a media, or sterile water. In other embodiments, the bacterial sample used is a bacterial cell suspension and the suspension is contacted with the tablet. In certain embodiments, the composition further comprises an agent that promotes the stabilization of the lysis reagent. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In one embodiment, presented herein are methods for detecting the presence of glucuronidase in a bacterial source utilizing a composition described herein in the form of a dry powder. In a specific embodiment, a method for detecting the presence of glucuronidase in a bacterial source comprises (a) contacting a bacterial sample with a composition in the form of a dry powder, wherein the composition comprises a lysis reagent and a glucuronidase substrate; and (b) detecting utilization of the substrate in the composition, wherein substrate utilization in the composition indicates the presence of glucuronidase in the bacterial source. In certain embodiments, the dry powder is hydrated prior to or concurrently with the step of contacting the bacterial sample with the dry powder. The dry powder may be hydrated using, e.g., a buffer, a saline buffer, a media, or sterile water. In other embodiments, the bacterial sample used is a bacterial cell suspension and the suspension is contacted with the dry powder. In certain embodiments, the composition further comprises an agent that promotes the stabilization of the lysis reagent. In other embodiments, the composition further comprises an agent that promotes the stabilization of the lysis reagent and an agent that enhances the lysis of a bacterial cell by a lysis reagent. In a specific embodiment, the composition further comprises a carbohydrate and EGTA or EDTA.

In a specific embodiment, the contacting step of the methods presented herein is conducted at about 20° C. to about 42° C., more preferably about 25° C. to about 40° C., and most preferably about 37° C. The detection step of the methods presented herein may be performed for the minimum amount of time needed for enough intracellular microorganism target detection reagent to be utilized by a microorganism sample positive for the presence of the intracellular microorganism target to allow detection by a standard method for a particular intracellular microorganism target detection reagent (e.g., visual observation and/or spectrophotometry for a chromogenic intracellular microorganism target detection reagent). In a specific embodiment, the detection step of the methods presented herein may be performed for the minimum amount of time needed for enough intracellular bacterial target detection reagent to be utilized by a bacterial sample positive for the presence of the intracellular bacterial target to allow detection by a standard method for a particular intracellular bacterial target detection reagent (e.g., visual observation and/or spectrophotometry for a chromogenic intracellular bacterial target detection reagent).

In some embodiments, in addition to a microorganism sample to be tested for the presence of an intracellular microorganism target, a microorganism sample that is known to express the intracellular microorganism target (i.e., a positive control) is included in the methods presented herein. In other embodiments, in addition to a microorganism sample to be tested for the presence of an intracellular microorganism target, a microorganism sample that is known to not express the intracellular microorganism target (i.e., a negative control) is included in the methods presented herein. In yet other embodiments, in addition to a microorganism sample to be tested for the presence of an intracellular microorganism target, a microorganism sample that is known to express the intracellular microorganism target (i.e., a positive control) and a microorganism sample that is known to not express the intracellular microorganism target (i.e., a negative control) are included in the methods presented herein. Positive and negative controls for the assays described herein may be identified using molecular and/or biochemical methods, such as sequencing, to determine the expression of an intracellular microorganism target by a particular microbe.

In some embodiments, in addition to a bacterial sample to be tested for the presence of an intracellular bacterial target, a bacterial sample that is known to express the intracellular bacterial target (i.e., a positive control) is included in the methods presented herein. In other embodiments, in addition to a bacterial sample to be tested for the presence of an intracellular bacterial target, a bacterial sample that is known to not express the intracellular bacterial target (i.e., a negative control) is included in the methods presented herein. In yet other embodiments, in addition to a bacterial sample to be tested for the presence of an intracellular bacterial target, a bacterial sample that is known to express the intracellular bacterial target (i.e., a positive control) and a bacterial sample that is known to not express the intracellular bacterial target (i.e., a negative control) are included in the methods presented herein. Positive and negative controls for the assays described herein may be identified using molecular and/or biochemical methods, such as sequencing, to determine the expression of an intracellular bacterial target by a particular bacterial strain.

Generally, the microorganism samples contacted with the different compositions utilized as part of the methods presented herein are from the same source. In one embodiment, the microorganism sample contains at least the minimum amount of microbe required to detect substrate utilization of an intracellular microorganism target reagent. In certain embodiments, a microorganism sample comprises at least $10^3$ colony forming units (CFU)/ml, preferably at least $10^5$ CFU/ml, more preferably at least $10^6$, and most preferably at least $10^7$ CFU/ml of microorganism. In other embodiments, a microorganism sample comprises about $10^3$ CFU/ml to about $10^{12}$ CFU/ml, about $10^5$ CFU/ml to about $10^{12}$ CFU/ml, about $10^6$ CFU/ml to about $10^{12}$ CFU/ml, or about $10^7$ CFU/ml to about $10^{12}$ CFU/ml of microorganism. In one embodiment, approximately the same number of microorganisms are in each microorganism sample contacted with a composition utilized in a method described herein.

Generally, the bacterial samples contacted with the different compositions utilized as part of the methods presented herein are from the same source. In one embodiment, the bacterial sample contains at least the minimum amount of bacteria required to detect substrate utilization of an intracellular bacterial target reagent. In a specific embodiment, a bacterial sample comprises at least $10^3$ colony forming units (CFU)/ml, preferably at least $10^5$ CFU/ml, more preferably at least $10^6$, and most preferably at least $10^7$ CFU/ml of bacteria. In another embodiment, a bacterial sample comprises about $10^3$ CFU/ml to about $10^{12}$ CFU/ml, about $10^5$ CFU/ml to about $10^{12}$ CFU/ml, about $10^6$ CFU/ml to about $10^{12}$ CFU/ml, or about $10^7$ CFU/ml to about $10^{12}$ CFU/ml of bacteria. In a particular embodiment, a bacterial sample comprises about $10^7$ CFU/ml to about $10^{10}$ CFU/ml of bacteria. In one embodiment, approximately the same number of bacteria are in each bacterial sample contacted with a composition utilized in a method described herein. In a specific embodiment, approximately the same amount of CFU are contacted with each of the compositions.

In some embodiments, a microorganism sample is a sample of microorganisms that is added to a buffer, sterile water or culture medium such as broth (e.g., AST broth or ID broth (BD, USA)) to make a cell suspension. In one embodiment, the same amount of the microbial suspension is contacted with each of the compositions. In a specific embodiment, the turbidity of the microbial suspension contacted with each composition is within an acceptable range for the device utilized to detect utilization of an intracellular microorganism target.

In specific embodiments, a bacterial sample is a sample of bacteria that is added to a buffer, sterile water or culture medium such as broth (e.g., AST broth or ID broth (BD, USA)) to make a cell suspension. In one embodiment, the same amount of the cell suspension is contacted with each of the compositions. In a specific embodiment, the turbidity of the cell suspension contacted with each composition is within an acceptable range for the device utilized to detect utilization of an intracellular bacterial target. In another embodiment, the turbidity of the cell suspension contacted with each of the compositions is about 0.1 to about 3, about 0.2 to about 2.5 or about 0.2 to about 2 as measured by a Dade Behring Microscan turbidity reader. In another embodiment, the turbidity of the cell suspension contacted with each of the compositions is about 0.1 to about 4, about 0.2 to about 5, or about 0.25 to about 4 MacFarland as measured by PhoenixSpec. In another embodiment, the turbidity of the cell suspension contacted with each of the compositions is about 0.1 to about 5, about 0.1 to about 4, about 0.2 Co about 5, or about 0.25 to about 4 MacFarland as measured by PhoenixSpec after being diluted about 5 to 10 times. In another embodiment, the turbidity of the cell suspension contacted with each of the compositions is about 0.4 to about 0.8, about 0.5 to about 0.7, or about 0.5 to about 0.6 MacFarland as measured by PhoenixSpec (BD, USA).

The detection step of the methods presented herein may be performed for the minimum amount of time needed for enough intracellular microorganism target detection reagent to be utilized by a microorganism sample positive for an intracellular microorganism target of interest to allow detection by a standard method for a particular intracellular microorganism target detection reagent (e.g., visual observation and/or spectrophotometry for a chromogenic reagents). In specific embodiments, the detection step of the methods presented herein may be performed for the minimum amount of time needed for enough intracellular bacterial target detection reagent to be utilized by a bacterial sample positive for an intracellular bacterial target of interest to allow detection by a standard method for a particular intracellular bacterial target detection reagent (e.g., visual observation and/or spectrophotometry for a chromogenic reagents).

In a particular embodiment, the detection step of the methods presented herein is performed about 2 minutes to about 60 minutes, preferably about 2 minutes to about 45 minutes or about 2 minutes to about 30 minutes, more preferably about 2 minutes to about 15 minutes, and most preferably about 2 minutes to about 10 minutes after the contacting step. In another embodiment, the detection step of the methods presented herein is performed about 15 minutes to about 5 hours, about 30 minutes to about 5 hours, about 30 minutes to about 4 hours, about 30 minutes to about 5 hours, about 1 hour to about 2 hours, about 1 hour to about 3 hours, about 1 hour to about 4 hours, about 1 hour to about 5 hours, about 2 hours to about 4 hours, about 2 hours to about 5 hours, or about 2 hours to about 6 hours after the contacting step. In another embodiment, the detection step of the methods presented herein is performed at different time points over about 24 hours, about 20 hours, about 18 hours, about 16 hours, about 12 hours, about 8 hours, about 4 hours, about 2 hours or about 1 hour. In some embodiments, the detection step is performed after each microorganism sample from the same source is contacted with each composition for the same amount of time. In a specific embodiment, the detection step is performed after each bacterial sample from the same source is contacted with each composition for the same amount of time.

In some embodiments, the rate of an utilization of intracellular microorganism target detection reagent when bacterial samples from the same source are contacted with different compositions is compared. The activity of different intracellular microorganism targets may be affected differently by the concentration of an intracellular microorganism target detection reagent included in a composition, the pH of the composition, and the temperature at which the contacting step is conducted.

In some embodiments, the rate of an utilization of intracellular bacterial target detection reagent when bacterial samples from the same source are contacted with different compositions is compared. In a specific embodiment, a spectrophotometer that has software to calculate the rate of utilization of an intracellular bacterial target detection reagent is used. The activity of different intracellular bacterial targets may be affected differently by the concentration of an intracellular bacterial target detection reagent included in a composition, the pH of the composition, and the temperature at which the contacting step is conducted.

In some embodiments, a qualitative difference between compositions is compared when determining utilization of an intracellular microorganism target detection reagent. In other embodiments, a quantitative difference between compositions is compared when determining utilization of an intracellular microorganism target detection reagent. The particular technique used to assess utilization of an intracellular microorganism target detection reagent will vary depending upon the intracellular microorganism target detection reagent chosen.

In some embodiments, a qualitative difference between compositions is compared when determining utilization of an intracellular bacterial target detection reagent. For example, qualitative differences between a composition to which a negative or positive control bacterial sample has been contacted relative to a composition to which a test bacterial sample has been contacted. In other embodiments, a quantitative difference between compositions is compared when determining utilization of an intracellular bacterial target detection reagent.

The particular technique used to assess utilization of an intracellular bacterial target detection reagent will vary depending upon the intracellular bacterial target detection reagent chosen. For example, if the intracellular bacterial target detection reagent is a chromogenic substrate, then utilization of the intracellular bacterial target detection reagent can be assessed by visual observation or spectrophotometry (at, e.g., a wavelength of 492 nm or 390 nm for nitrocefin). If the intracellular bacterial target detection reagent is a fluorogenic substrate, then utilization of the intracellular bacterial target detection reagent can be detected by measuring the fluorescence of the substrate. Different antibiotics have different wavelengths and the use of an antibiotic as an intracellular bacterial target detection reagent by a bacterial species will result in a change in the wavelength of the composition. Thus, in some embodiments, a spectrophotometer is used to monitor changes in the wavelength of a composition comprising an antibiotic as the intracellular bacterial target detection reagent.

In specific embodiments, the BD Phoenix™ Automated Microbiology System (BD, USA) is used to assess utilization of an intracellular bacterial target detection reagent. In other embodiments, a Vitek® automated system (bioMerieux, USA) is used to assess utilization of an intracellular bacterial target detection reagent. In other embodiments, a MicroScan Walk-Away® automated system (Dade Behring, USA) is used to assess utilization of an intracellular bacterial target detection reagent.

4.4 Samples 4.4.1 Microorganism Samples

A microorganism sample isolated, obtained or derived from a biological sample from any source can be used in the methods presented herein. In one embodiment, a microorganism sample is isolated, obtained or derived from a biological sample obtained from a subject, e.g., a human subject. Examples of subjects from which such a biological sample may be obtained and utilized in accordance with the methods presented herein include, but are not limited to, asymptomatic subjects, subjects manifesting or exhibiting 1, 2, 3, 4 or more symptoms of an infection, subjects clinically diagnosed as having an infection, subjects predisposed to infections (e.g., subjects with a genetic predisposition to infections, and subjects that lead a lifestyle that predisposes them to infections or increases the likelihood of contracting an infection), subjects suspected of having an infection, subjects undergoing therapy for an infection, subjects with an infection and at least one other condition (e.g., subjects with 2, 3, 4, 5 or more conditions), subjects not undergoing therapy for an infection, and subjects that have not been diagnosed with an infection. In one embodiment, the infection is a fungal infection. In another embodiment, the infection is a parasite infection. In another embodiment, the infection is a bacterial infection.

Non-limiting examples of fungus that cause infections include *Blastomyces*, including *Blastomyces dermatitidis; Paracoccidiodes*, including *Paracoccidioides brasiliensis; Sporothrix*, including *Sporothrix schenckii; Cryptococcus; Candida*, including *Candida albicans, Candida tropicalis* and *Candida glabrala; Aspergillus*, including *Aspergillus fumigarus* and *Aspergillus flavus; Histoplasma*, including *Histoplasma capsulatum; Cryptococcus*, including *Cryptococcus neoformans; Bipolaris; Cladophialophora; Cladosporium; Drechslera; Exophiala; Fonsecaea; Phialophora; Xylohypha; Ochroconis; Rhinocladiella; Scolecobasidium*; and *Wangiella*. Non-limiting examples of parasites that cause infections include *B. divergens, B. bigemina, B. equi, B. microfii, B. Duncani, Balantidium coli, Cryptosporidium, Blastocystis, Dientamoeba fragilis, Entamoeba histolytica, Leishmania, Plasmodium falciparum, Trichomonas vaginalis, Trypanosoma brucei, Trypanosoma cruzi*, and *Schistosoma mansoni*.

A biological sample can be obtained from any tissue or organ in a subject, or a secretion from a subject. Representative biological samples from a subject include, without limitation, nasal swabs, throat swabs, feces, dermal swabs, blood (including blood culture), sputum, salvia, bronchioalveolar lavage, bronchial aspirates, lung tissue, spinal fluid, synovial fluid and urine. In some embodiments, two, three or more biological samples are obtained from a subject. In specific embodiments, two or more biological samples are obtained from two or more tissues, organs and/or secretions from a subject. In addition to obtaining a biological sample from a subject, a biological sample may be obtained from food, a beverage, a phone, a counter, etc. Techniques for collecting biological samples are known to those of skill in the art.

In some embodiments, a biological sample is stored before use. For example, a biological sample from a subject can be stored at 4° C., −30° C. or −70° C. Techniques for storing biological samples are known to one of skill in the art.

In some embodiments, after a biological sample is obtained, the biological sample can be processed so that a pure microorganism sample is obtained or the biological sample can be stored before processing using techniques known to one of skill in the art. Any technique known to one of skill in the art may be used to obtain a pure microorganism sample. In certain embodiments, a pure microorganism sample is used within 24 hours as a bacterial sample. In some embodiments, a pure microorganism sample is stored before use (e.g., at 4° C. or −70° C.). Techniques for storing microorganism samples are known to one of skill in the art. In some embodiments, an aliquot or inoculum of the pure microorganism sample is used as a microorganism sample.

In certain embodiments, after obtaining biological sample, any microorganism present in the sample can be proliferated before it is used in accordance with the methods described herein. In other embodiments, after obtaining a biological sample, the biological sample can be used to inoculate media and the inoculated media is incubated for a certain period of time to allow any microorganism present in the sample to proliferate. The media chosen as well as the growth conditions (e.g., temperature will depend upon the bacteria being collected). In some embodiments, the microorganism culture is stored before use (e.g., at 4° C. or −70° C.). Techniques for storing microorganism cultures are known to one of skill in the art. In some embodiments, an aliquot or inoculum of the microbes in the culture is used as a microorganism sample.

In some embodiments, a microorganism sample is stored before use. For example, a microorganism sample is stored at 4° C.

In certain embodiments, a sample of microbes isolated, obtained or derived from any source is added to a buffer to make a cell suspension and an aliquot of the cell suspension is used as a microorganism sample. In some embodiments, a sample of microbes isolated, obtained or derived from any source is added to sterile water to make a cell suspension and an aliquot of the cell suspension is used as a microorganism sample. In specific embodiments, a sample of microbes isolated, obtained or derived from any source is added to broth or saline buffer to make a microbial suspension and an aliquot of the microbial suspension is used as a microorganism sample.

In certain embodiments, a pure microorganism sample is added to a buffer to make a microbial suspension and an aliquot of the microbial suspension is used as a bacterial sample. In some embodiments, a pure microorganism sample is added to sterile water to make a microbial suspension and an aliquot of the microbial suspension is used as a microorganism sample. In a particular embodiment, the pure microorganism sample is added to the buffer, sterile water, broth or saline buffer within 24 hours or less of the generation of the pure microorganism sample.

4.4.2 Bacterial Samples

A bacterial sample isolated, obtained or derived from a biological sample from any source can be used in the methods presented herein. In one embodiment, a bacterial sample is isolated, obtained or derived from a biological sample obtained from a subject, e.g., a human subject. Examples of subjects from which such a biological sample may be obtained and utilized in accordance with the methods presented herein include, but are not limited to, asymptomatic subjects, subjects manifesting or exhibiting 1, 2, 3, 4 or more symptoms of an infection, subjects clinically diagnosed as having an infection, subjects predisposed to infections (e.g., subjects with a genetic predisposition to infections, and subjects that lead a lifestyle that predisposes them to infections or increases the likelihood of contracting an infection), subjects suspected of having an infection, subjects undergoing therapy for an infection, subjects with an infection and at least one other condition (e.g., subjects with 2, 3, 4, 5 or more conditions), subjects not undergoing therapy for an infection, and subjects that have not been diagnosed with an infection. In one embodiment, the infection is a gram negative bacterial infection. In another embodiment, the infection is a gram positive bacterial infection. Non-limiting examples of bacteria that cause bacterial infections include *E. coli, Klebsiella* (e.g., *Klebsiella pneumoniae* and *Klebsiella oxytoca*), *Staphylococcus* (e.g., *Staphylococcus aureus*), *Streptococcus* (e.g., *Streptococcus pneumoniae*), *Haemophilus influenzae, Neisseria gonorrhoeae, Pseudomonas* (e.g., *Pseudomonas aeruginosa*), *Enterococcus* and *Acinetobacter baumannii*.

In one embodiment, the subject is a mammal such as a non-primate (e.g., a cow, dog, pig, cat, dog, horse, etc.) and a primate (e.g., a human). In another embodiment, the subject is a non-human animal, such as a bird, reptile, and a non-human mammal. In another embodiment, the subject is a farm animal (e.g., a pig, horse, or cow), a pet (e.g., a guinea pig, dog, or cat) and/or a laboratory animal (e.g., a rat or mouse). In a preferred embodiment, the subject is a human.

A biological sample can be obtained from any tissue or organ in a subject, or a secretion from a subject. Representative biological samples from a subject include, without limitation, nasal swabs, throat swabs, feces, dermal swabs, blood (including blood culture), sputum, salvia, bronchio-alveolar lavage, bronchial aspirates, lung tissue, spinal fluid, synovial fluid and urine. In some embodiments, two, three or more biological samples are obtained from a subject. In specific embodiments, two or more biological samples are obtained from two or more tissues, organs and/or secretions from a subject. In addition to obtaining a biological sample from a subject, a biological sample may be obtained from food, a beverage, a phone, a counter, etc. Techniques for collecting biological samples are known to those of skill in the art.

In some embodiments, a biological sample is stored before use. For example, a biological sample from a subject can be stored at 4° C., −30° C. or −70° C. Techniques for storing biological samples are known to one of skill in the art.

In some embodiments, after a biological sample is obtained, the biological sample can be processed so that a pure bacterial sample is obtained or the biological sample can be stored before processing using techniques known to one of skill in the art. Any technique known to one of skill in the art may be used to obtain a pure bacterial sample. Generally, a biological sample is streaked onto a solid agar-containing medium so as to separate the bacterial population present in the biological sample into individual cells that grow as individual colonies. The media chosen as well as the growth conditions (e.g., the temperature and gases in the environment) will depend upon the bacteria being selected. For example, Trypticase™ Soy Agar with 5% sheep blood (BD, USA), incubated at 35° C. for 18 hours may be used to obtain individual bacterial colonies. In certain embodiments, a pure bacterial sample is used within 24 hours as a bacterial sample. In some embodiments, a pure bacterial sample is stored before use (e.g., at 4° C. or −70° C.). Techniques for storing bacterial samples are known to one of skill in the art. In some embodiments, an aliquot or inoculum of the pure bacterial sample is used as a bacterial sample.

In other embodiments, after obtaining a biological sample, the biological sample can be used to inoculate media and the inoculated media is incubated for a certain period of time to allow any bacteria present in the sample to proliferate. The media chosen as well as the growth conditions (e.g., temperature will depend upon the bacteria being collected). For example, Trypticase™ Soy Broth (BD, USA) or Trypticase™ Soy Agar with 5% sheep blood (BD, USA), incubated at 35° C. for 18 hours may be used. In some embodiments, the bacterial culture is stored before use (e.g., at 4° C. or −70° C.). Techniques for storing bacterial cultures are known to one of skill in the art. In some embodiments, an aliquot or inoculum of the bacteria in the culture is used as a bacterial sample.

In some embodiments, a bacterial sample is stored before use. For example, a bacterial sample is stored at 4° C.

In certain embodiments, a sample of bacteria isolated, obtained or derived from a biological sample from any source is added to a buffer to make a cell suspension and an aliquot of the cell suspension is used as a bacterial sample. In some embodiments, a sample of bacteria isolated, obtained or derived from a biological sample from any source is added to sterile water to make a cell suspension and an aliquot of the cell suspension is used as a bacterial sample. In specific embodiments, a sample of bacteria isolated, obtained or derived from a biological sample from any source is added to broth or saline buffer (e.g., AST broth or ID broth sold as part of a kit for the BD Phoenix™ Automated Microbiology System (BD, USA)) to make a cell suspension and an aliquot of the cell suspension is used as a bacterial sample.

In certain embodiments, a pure bacterial sample is added to a buffer to make a cell suspension and an aliquot of the cell suspension is used as a bacterial sample. In some embodiments, a pure bacterial sample is added to sterile water to make a cell suspension and an aliquot of the cell suspension is used as a bacterial sample. In specific embodiments, a pure bacterial sample is added to a broth or saline buffer (e.g., AST broth or ID broth sold as part of a kit for BD Phoenix™ Automated Microbiology System (BD, USA)) to make a cell suspension and an aliquot of the cell suspension is used as a bacterial sample. In a particular embodiment, the pure bacterial sample is added to the buffer, sterile water, broth or saline buffer within 24 hours or less of the generation of the pure bacterial sample.

In some embodiments, a bacterial sample comprises either a gram negative bacteria or a gram positive bacteria, or both. In some embodiments, a bacterial sample comprises a *Mycobacteria*.

4.5 Characterization of Microorganisms

In addition to or in conjunction with the detection of the presence of an intracellular microorganism target, a microorganism sample can be characterized using techniques known to one of skill in the art. For example, a sample may be observed for the morphology of the microorganism and/or different staining reactions may be performed to characterize the microorganism. The morphological characteristics and staining reactions can aid in the identification of the microorganism.

In a specific embodiment, in addition to or in conjunction with the detection of the presence of an intracellular bacterial target, a bacterial sample can be characterized using techniques known to one of skill in the art. For example, a bacterial sample may be observed for the morphology of the bacteria and/or different staining reactions may be performed. The morphological characteristics and staining reactions can aid in the identification of the bacteria. In a specific embodiment, a gram stain is performed using techniques known to one of skill in the art. In certain embodiments, the gram stain is performed before the detection of the presence of an intracellular bacterial target. In another embodiment, an assay to identify the species of bacteria is performed using techniques known to one of skill in the art. In a specific embodiment, an ID run on an automated antibiotic susceptibility instrument, such as the BD Phoenix ID/AST System, is performed to identify the species of bacteria.

4.6 Selection of Therapy

Detection of the presence of a specific intracellular microorganism target (e.g., an intracellular bacterial target) utilizing the methods presented herein can, for example, provide information for the selection of an appropriate therapeutic regimen for a patient diagnosed with microbial (e.g., a bacterial) infection. For example, detecting the presence of a specific intracellular bacterial target in a bacterial source may indicate what antibiotics should not be used to treat an infection caused by the bacteria and suggest alternative therapies, e.g., drugs that the bacteria is not resistant to. In addition to facilitating the appropriate therapeutic regimen for a patient, the detection of the presence of a specific intracellular microorganism target (e.g., an intracellular bacterial target) in a microbial source (e.g., a bacterial source) may aid in reducing the transmission of the intracellular microorganism target (e.g., an intracellular bacterial target) to other microbes (e.g., bacteria) and/or reduce the spread of the microbe (e.g, bacteria).

4.7 Quality Control

Detection of the presence a specific intracellular microorganism target (e.g., an intracellular bacterial target) can provide information regarding the quality of commercial products, e.g., food products, beverage products, pharmaceutical products, cosmetics products, etc. In certain embodiments, the methods provided herein can be used to determine whether a commercial product meets a certain standard of manufacture.

In some embodiments, a commercial product is monitored for the presence a specific intracellular microorganism target (e.g., an intracellular bacterial target) throughout the manufacturing process of the commercial product. In accordance with such embodiments, the commercial product may be analyzed with one or more of the methods described herein at the beginning of the period of manufacture; at one or more times during the period of manufacture; and/or at the end of the period of manufacture. One or more of the methods described herein could be used as many times as necessary to monitor the commercial product as it is being produced.

4.8 Kits

Presented herein are kits comprising, in a container, a solid support containing a dried form of a composition described herein. The dried form of the composition may be present in or on a solid support. In certain embodiments, the solid support is a well of a panel, tray, cassette or plate (e.g., a microtiter plate). In specific embodiments, the solid support is a well of a Phoenix™ Panel (BD, USA), a well of a panel of a BBL™ Crystal™ (Identification System (BD, USA), a Vitek® card (bioMerieux, USA), a well of a MicroScan panel (Dade Behring, USA), or a well of a panel of a Remel RapID™ System (Remel, USA). See, e.g., U.S. Pat. Nos. 5,922,593 and Des. 421,498 (each of which are incorporated herein by reference) for an exemplary description of panels with wells that may be used. In other embodiments, the solid support is a tube, e.g., a test tube or eppendorf. In certain embodiments, the solid support is a tube of an API biochemical test (bioMerieux, USA).

In one embodiment, presented herein are kits comprising a paper disk or paper strip containing a dried form of a composition described herein. In certain embodiments, a paper disk or paper strip is divided up into different sections with each section comprising a different composition. In another embodiment, there is only one composition per paper disk or paper strip. In a specific embodiment, the paper disk or paper strip is filter paper. In another specific embodiment, presented herein are kits comprising a solid support similar to BBL™ Dryslide™ Nitrocefin (Becton Dickinson, Diagnostic Systems, USA) containing a dried form of a composition described herein.

In certain embodiments, presented herein are kits comprising a panel, tray, cassette or plate (e.g., a microtiter) with one or more wells in which one or more compositions described herein is dried and is present. In some embodiments, different wells of a panel, tray, cassette or plate have a different composition. In specific embodiments, presented herein are kits comprising a Phoenix™ Panel (BD, USA), a panel of a BBL™ Crystal™ Identification System (BD, USA), a Vitek® card (bioMerieux, USA), a MicroScan panel (Dade Behring, USA), or a panel of a Remel RapID™ System (Remel, USA) in which one or more of the wells of the panels have present a dried form of one or more compositions described herein. See, e.g., U.S. Pat. Nos. 5,922,593 and Des. 421,498 (each of which are incorporated herein by reference) for an exemplary description of panels with wells that a composition described herein may dried in and may be used in the kits presented herein.

In certain embodiments, presented herein are kits comprising a tube, e.g., a test tube or eppendorf, in which a dried from of a composition described herein is present. In specific embodiments, presented herein are kits comprising, in a container, a tube of an API biochemical test (bioMerieux, USA) in which a dried form of a composition described herein is present.

In certain embodiments, presented herein are kits comprising tablet, wherein the tablet comprises a composition described herein. In some embodiments, presented herein are kits comprising a composition described herein in the form of a dry powder.

In some embodiments, the kits presented herein comprise a buffer, saline buffer, or a broth to resuspend microorganisms, e.g., a pure microorganism sample. In specific embodiments, the kits presented herein comprise a buffer, saline buffer, or a broth to resuspend bacteria, e.g., a pure bacterial sample.

The kits presented herein may comprise instructions for using the kits to detect the presence of an intracellular microorganism target. In particular embodiments, the kits presented herein may comprise instructions for using the kits to detect the presence of an intracellular bacterial target. In a specific embodiment, the instructions recommend that positive and negative controls are run in parallel with test samples.

In some embodiments, the kits presented herein comprise a microorganism sample that is known to not express an intracellular microorganism target (i.e., a negative control). In other embodiments, the kits presented herein comprise a microorganism sample that is known to express an intracellular microorganism target (i.e., a positive control). In yet other embodiments, the kits presented herein comprise a microorganism sample that is known to express an intracellular microorganism target (i.e., a positive control) and a microorganism sample that is known to not express an intracellular bacterial target (i.e., a negative control).

In some embodiments, the kits presented herein comprise a bacterial sample that is known to not express an intracellular bacterial target (i.e., a negative control). In other embodiments, the kits presented herein comprise a bacterial sample that is known to express an intracellular bacterial target (i.e., a positive control). In yet other embodiments, the kits presented herein comprise a bacterial sample that is known to express an intracellular bacterial target (i.e., a positive control) and a bacterial sample that is known to not express an intracellular bacterial target (i.e., a negative control).

4.9 Systems

Presented herein are systems comprising a kit or a component(s) of the kits presented herein and a computer program product for use in conjunction with a computer system. In such systems, the computer program product can comprise a computer readable storage medium and a computer program mechanism embedded therein. The computer program mechanism may comprise instructions for evaluating the presence of a particular intracellular microorganism target (e.g., an intracellular bacterial target), in one or a plurality of microorganism samples (e.g., bacterial samples).

In a specific embodiment, the system used for evaluating the presence of an intracellular microorganism target (e.g., an intracellular bacterial target) is the same or similar to the BD Phoenix™ Automated Microbiology System (BD, USA). See, e.g., U.S. Pat. Nos. 5,922,593, 6,096,272, 6,372, 485, and 7,115,384 (each of which are incorporated herein by reference) for a description of such an automated system. In another embodiment, the system used for evaluating the presence of an intracellular microorganism target (e.g., an intracellular bacterial target) is the same or similar to the Vitek® automated system from bioMerieux. In another embodiment, the system used for evaluating the presence of an intracellular microorganism target (e.g., an intracellular bacterial target) is the same or similar to the MicroScan Walk-Away® automated system from Dade Behring.

Some systems presented herein comprise a kit or one or more components of the kits presented herein, a computer having a central processing unit and a memory coupled to the central processing unit. Some systems presented herein comprise a kit or one or more components of the kits presented herein, a computer readable medium (such as a handheld fluorometer or spectrophotometer), a computer having a central processing unit and a memory coupled to the central processing unit. The memory stores instructions for evaluating the presence of a particular intracellular microorganism target (e.g., intracellular bacterial target). En some embodiments, the memory comprises instructions for transmitting the results of a method presented herein to a remote computer and the remote computer includes instructions for evaluating there presence of one, two, three or more intracellular microorganism targets (e.g., intracellular bacterial targets).

In some embodiments, presented herein is a computer system comprising a computer readable medium comprising the results of an evaluation for the presence of a particular intracellular microorganism target (e.g., an intracellular bacterial target). In some embodiments, a computer system presented herein comprises:

a central processing unit;

a main non-volatile storage unit, for example, a hard disk drive, for storing software and data, the storage unit controlled by storage controller;

a system memory, such as high speed random-access memory (RAM), for storing system control programs, data and application programs, comprising programs and data loaded from non-volatile storage unit, and may also include a read-only memory (ROM);

a user interface, comprising one or more input devices (e.g., a keyboard) and display or other output device;

a network interface card for connecting to any wired or wireless communication network (e.g., a wide area network such as the Internet);

an internal bus for interconnecting the aforementioned elements of the system; and a power source to power the aforementioned elements. Operation of the computer can be controlled primarily by an operating system, which is executed by a central processing unit. The operating system can be stored in the system memory. In addition to the operating system, an implementation system may include: a file system for controlling access to the various files and data structures presented herein; a training data set for use in the construction of one or more decision rules in accordance with the methods presented herein; a data analysis algorithm module for processing training data and constructing decision rules; one or more decision rules; a profile evaluation module for determining whether a particular intracellular bacterial target is present.

The computer may comprise software program modules and data structures. Each of the data structures can comprise any form of a data storage system, including, but not limited to, a flat ASCII or binary file, an Excel spreadsheet, a relational database (e.g., SQL), or an on-line analytical processing (OLAP) database (e.g., MDX and/or variants thereof). In some embodiments, such data structures are each in the form of one or more databases that include a hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to the computer system are single data structures. In other embodiments, such data structures in fact comprise a plurality of data structures (e.g., databases, files, archives) that may or may not all be hosted by the same computer. For example, in some embodiments, a training data set may comprise a plurality of Excel spreadsheets that are stored either on the computer and/or computers that are addressable by the computer across wide area network. In another example, a training set may comprise a database that is either stored on the computer or is distributed across one or more computers that are addressable by the computer across a wide area network.

It will be appreciated that many of the modules and data structures mentioned above can be located on one or more remote computers. For example, in some embodiments, web service-type implementations are used. In such embodiments, an evaluation module can reside on a client computer that is in communication with the computer via a network. In some embodiments, a profile evaluation module can be an interactive web page.

In some embodiments, a training data set and/or decision rules are on a single computer and in other embodiments, one or more of such data structures and modules are hosted by one or more remote computers. Any arrangement of the data structures and software modules on one or more computers is within the scope the systems presented herein so long as these data structures and software modules are addressable with respect to each other across a network or by other electronic means.

In some embodiments, a digital signal embodied on a carrier wave comprises data with respect to a method presented herein. In some embodiments, a digital signal embodied on a carrier wave comprises a determination as to whether a particular intracellular microorganism target (e.g., an intracellular bacterial target) is present in a bacterial source. In some embodiments, a graphical user interface is provided for determining whether a beta-lactamase or other enzyme is present in a bacterial source. The graphical user interface may comprise a display field for displaying a result encoded in a digital signal embodied on a carrier wave received from a remote computer.

5. EXAMPLE

This example demonstrates that the in situ lysis of bacterial cells and the detection of an intracellular bacterial target provides a high level of sensitivity of the assay, which can be particularly advantageous when detecting certain intracellular bacterial targets expressed by certain types of bacteria (e.g., gram negative bacteria).

5.1 Materials and Methods

Panel production. Stock solutions with nitrocefin, trehalose, and/or reagents used to lyse the bacterial cells in pH6 MES buffer were prepared and dispensed into wells on the bottom part of a Phoenix™ panel (BD, USA), with one stock solution in one well. Panels were then dried in an oven for approximately 30 min at approximately 70° C. The top part of Phoenix panel was then attached to the bottom part forming a panel system ready for inoculation. The concentrations of reagents after rehydration following Phoenix panel inoculation were 3 mg/ml lysozyme, 1 mM EDTA, and 1% trehalose in 0.1M pH6 MES buffer.

Inoculation and lysis testing. Representative strains of bacteria, such as *E. coli* and *Klebsiella pneumoniae*, were each streaked on a Trypticase™ Soy Agar with 5% Sheep Blood agar plate (BD, USA) and the plates were incubated at 35° C. for 18 hours. Afterwards, colonies from pure culture on each plate were inoculated into BD Phoenix ID broth and adjusted to a desired turbidity of approximately 0.5 MacFarland. The bacterial cell suspension was then poured into the ID side of the Phoenix panels that were specifically made for cell lysis testing. Once inoculated, the panel was loaded into Phoenix instrument, where nitrocefin hydrolysis rate was monitored by colorimetric signals changes every 20 minutes for 16 hours.

Microorganism. The presence of beta-lactamase in the strains tested herein was previously characterized by isoelectric focusing (IEF) gel electrophoresis, PCR testing, or MIC assays, which were performed by microbroth dilution method according to the CLSI (Clinical and Laboratory Standards Institute) standard.

5.2 Results

As shown in Table 1, below, some strains that harbor intracellular beta-lactamase have relatively low nitrocefin activity (<=4 within 10 hrs on Phoenix panel) in the absence of lysis reagents. The addition of lysis reagents in Phoenix wells significantly improved the nitrocefin hydrolysis rate by those cells. Some strains exhibited relatively high nitrocefin activity (>4 within 10 hrs on Phoenix panel) in the absence of lysis reagents. With respect to those strains, the presence of lysis reagents did not result in a change or only resulted in a slight improvement in the nitrocefin activity. The lysis reagents did not inhibit the nitrocefin activity of the beta-lactamases expressed by the bacterial strains. Neither lysozyme nor EDTA, alone or in combination, hydrolyzed nitrocefin. Without being bound by any theory, it is believed that the improvement in the nitrocefin hydrolysis rate is primarily because more beta-lactamase is released from periplasmic space, and thus, more beta-lactamase is accessible to its substrate, nitrocefin.

TABLE 1

| Sample | Organism | Presence of intracellular beta-lactamase | NCF activity | NCF activity with lysis reagent |
|---|---|---|---|---|
| 1 | E. coli | + | 1.9 | 7.2 |
| 2 | E. coli | + | 2.1 | 7.7 |
| 3 | E. coli | + | 2.3 | 8.1 |
| 4 | E. coli | + | 1.9 | 6.8 |
| 5 | E. coli | + | 8.2 | 9.1 |
| 6 | E. coli | + | 7.2 | 8.1 |
| 7 | E. coli | + | 6.8 | 8.4 |
| 8 | E. coli | − | 1.7 | 1.8 |
| 9 | Klebsiella pneumoniae | + | 1.3 | 4.6 |
| 10 | Klebsiella pneumoniae | + | 3.3 | 6.3 |
| 11 | Klebsiella pneumoniae | + | 3.9 | 6.1 |
| 12 | Klebsiella pneumoniae | + | 2.6 | 5.6 |
| 13 | Klebsiella pneumoniae | + | 6.7 | 6.8 |
| 14 | Klebsiella pneumoniae | + | 7.5 | 8.8 |
| 15 | Klebsiella pneumoniae | + | 9.1 | 9.5 |
| 16 | Klebsiella pneumoniae | − | 1.2 | 1.8 |

NCF activity, the value shown is the maximum nitrocetin hydrolysis rate within 10 hrs following Phoenix panel loading into the instrument. The unit of activity is calculated based on Phoenix signals.

Equivalents

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. A bacterial enzyme detection assay component comprising a solid support containing a dried composition, wherein the dried composition comprises a lysis reagent and an intracellular bacterial target detection reagent, wherein the intracellular bacterial target detection reagent is a substrate for an intracellular bacterial enzyme, and wherein the amount of lysis reagent and intracellular bacterial target detection reagent in the dried composition are such that after rehydration with a single volume of liquid containing bacterial cells, the concentration of the lysis reagent and the intracellular bacterial target detection reagent in the single volume of liquid can be used to lyse the bacterial cells and detect the intracellular bacterial enzyme in the single volume of liquid, wherein the intracellular bacterial enzyme is not a beta-lactamase.

2. A bacterial enzyme detection assay component comprising a solid support containing a dried composition, wherein the dried composition comprises a lysis reagent, an intracellular target bacterial detection reagent, and a carbohydrate, wherein the intracellular bacterial target detection reagent is a substrate for an intracellular bacterial enzyme, and wherein the amount of lysis reagent and intracellular bacterial target detection reagent in the dried composition are such that after rehydration with a single volume of liquid containing bacterial cells, the concentration of the lysis reagent and the intracellular bacterial target detection reagent in the single volume of liquid can be used to lyse the bacterial cells and detect the intracellular bacterial enzyme in the single volume of liquid, wherein the intracellular bacterial enzyme is not a beta-lactamase.

3. A bacterial enzyme detection assay component comprising a solid support containing a dried composition, wherein the dried composition comprises lysozyme, trehalose, ethylenediaminetetraacetic acid ("EDTA"), and an intracellular bacterial target detection reagent, wherein the intracellular bacterial target detection reagent is a substrate for an intracellular bacterial enzyme, and wherein the amount of lysis reagent and intracellular bacterial target detection reagent in the dried composition are such that after rehydration with a single volume of liquid containing bacterial cells, the concentration of the lysis reagent and the intracellular bacterial target detection reagent in the single volume of liquid can be used to lyse the bacterial cells and detect the intracellular bacterial enzyme in the single volume of liquid, wherein the intracellular bacterial enzyme is not a beta-lactamase.

4. The bacterial enzyme detection assay component of claim 1, wherein the dried composition further comprises an agent that promotes the stabilization of the lysis reagent.

5. The bacterial enzyme detection assay component of claim 1, wherein the dried composition further comprises an agent that enhances the lysis of the bacterial cells by the lysis reagent.

6. The bacterial enzyme detection assay component of claim 1, wherein the lysis reagent is lysozyme, labiase, lysostaphin, achromopeptidase or mutanolysin.

7. The bacterial enzyme detection assay component of claim 1, wherein the dried composition further comprises an agent that promotes the stabilization of the lysis reagent and an agent that enhances the lysis of the bacterial cells by the lysis reagent.

8. The bacterial enzyme detection assay component of claim 1, wherein the intracellular bacterial enzyme is a peptidase, esterase, glucose oxidase, beta-glucosidase, or glucuronidase.

9. The bacterial enzyme detection assay component of claim 6, wherein the intracellular bacterial enzyme is a peptidase, esterase, glucose oxidase, beta-glucosidase, or glucuronidase.

10. The bacterial enzyme detection assay component of claim 1, wherein the solid support is a well of a tray, plate, panel or cassette.

11. The bacterial enzyme detection assay component of claim 1, wherein the solid support is a paper disk, a paper strip or a tube.

12. The bacterial enzyme detection assay component of claim 2, wherein the carbohydrate is mannitol, ribose, glucose, fructose, mannose, sucrose, glycerol, Xanthan gum, trehalose, or glycol.

13. The bacterial enzyme detection assay component of claim 2, wherein the intracellular bacterial enzyme is a peptidase, esterase, glucose oxidase, beta-glucosidase, or glucuronidase.

14. The bacterial enzyme detection assay component of claim 2, wherein the lysis reagent is lysozyme, labiase, lysostphin, achromopeptidase or mutanolysin.

15. The bacterial enzyme detection assay component of claim 13, wherein the lysis reagent is lysozyme, labiase, lysostphin, achromopeptidase or mutanolysin.

16. The bacterial enzyme detection assay component of claim 2, wherein the dried composition further comprises an agent that enhances the lysis of the bacterial cells by the lysis reagent.

17. The bacterial enzyme detection assay component of claim 16, wherein the agent is a metal chelator.

18. The bacterial enzyme detection assay component of claim 16, wherein the agent is EDTA or ethyleneglycol-bis (β-aminoethyl)-N,N,N',N'-tetraacetic acid ("EGTA").

19. The bacterial enzyme detection assay component of claim 2, wherein the solid support is a well of a tray, plate, panel or cassette.

20. The bacterial enzyme detection assay component of claim 2, wherein the solid support is a paper disk, a paper strip or a tube.

21. The bacterial enzyme detection assay component of claim 3, wherein the intracellular bacterial enzyme is a peptidase, esterase, glucose oxidase, beta-glucosidase, or glucuronidase.

22. The bacterial enzyme detection assay component of claim 3, wherein the solid support is a well of a tray, plate, panel or cassette.

23. The bacterial enzyme detection assay component of claim 3, wherein the solid support is a paper disk, a paper strip or a tube.

* * * * *